US007723473B2

(12) United States Patent
Huang

(10) Patent No.: US 7,723,473 B2
(45) Date of Patent: May 25, 2010

(54) PEPTIDE ANTAGONISTS OF TGF-BETA FAMILY MEMBERS AND THERAPEUTIC USES THEREOF

(75) Inventor: Jung San Huang, St. Louis, MO (US)

(73) Assignee: St. Louis University, St. Louis, MO (US)

( * ) Notice: Subject to any disclaimer, the term of this patent is extended or adjusted under 35 U.S.C. 154(b) by 215 days.

(21) Appl. No.: 11/432,125

(22) Filed: May 11, 2006

(65) Prior Publication Data

US 2006/0233708 A1    Oct. 19, 2006

Related U.S. Application Data

(63) Continuation of application No. 10/135,946, filed on Apr. 29, 2002, now abandoned, which is a continuation-in-part of application No. 09/095,637, filed on Jun. 11, 1998, now Pat. No. 6,500,920.

(60) Provisional application No. 60/050,202, filed on Jun. 19, 1997, now abandoned.

(51) Int. Cl.
  *C07K 14/00*    (2006.01)
  *C07K 14/495*   (2006.01)
  *C07K 14/765*   (2006.01)
(52) U.S. Cl. ................ 530/324; 530/363; 530/402; 530/815
(58) Field of Classification Search ................ None
  See application file for complete search history.

(56) References Cited

U.S. PATENT DOCUMENTS

| 4,179,337 | A | * | 12/1979 | Davis et al. ........... 435/181 |
| 4,423,037 | A |   | 12/1983 | Rosenblatt et al. |
| 4,456,596 | A |   | 6/1984  | Schafer |
| 4,959,314 | A |   | 9/1990  | Mark et al. |
| 5,444,151 | A |   | 8/1995  | Vassbotn et al. |
| 5,571,714 | A |   | 11/1996 | Dasch et al. |
| 5,654,270 | A |   | 8/1997  | Ruoslahti et al. |
| 5,981,606 | A |   | 11/1999 | Martin |
| 6,316,258 | B1 |  | 11/2001 | Noble et al. |
| 6,500,920 | B1 | * | 12/2002 | Haung .................. 530/328 |
| 6,906,026 | B1 |  | 6/2005  | Noble et al. |
| 7,057,013 | B1 |  | 6/2006  | Ezquerro Saenz et al. |

FOREIGN PATENT DOCUMENTS

| EP | 0433225 | 6/1991 |
| EP | 1132403 | 11/1996 |
| WO | WO 97/08196 A1 * | 3/1997 |
| WO | WO 00 31135 | 6/2000 |
| WO | WO 03 93293 | 11/2003 |

OTHER PUBLICATIONS

Derynck et al. Human transforming growth factor-beta complementary DNA sequence and expression in normal and transformed cells. Nature. Aug. 22-28, 1985;316(6030):701-5.*

Limbird, L.L. "Identification of Receptors Using Direct Radioligand Binding Techniques," Chapter 3 in Cell Surface Receptors: A Short Course on Theory and Methods, 2nd ed., Kluwer Academic Publishers, Massachusetts, 1996, pp. 61-65.*

Ngo et al., in The Protein Folding Problem and Tertiary Structure Prediction, Merz and Le Grand (Eds), Aug. 1994, Springer Verlag, pp. 433 and 492-495.*

Bowie et al. Deciphering the message in protein sequences: tolerance to amino acid substitutions. Science, (Mar. 16, 1990) 247 (4948) 1306-10.*

Ngo et al., in The Protein Folding Problem and Tertiary Structure Prediction, Merz and Le Grand (Eds), Aug. 1994, Springer Verlag, pp. 433 and 492-495.*

Burmester et al., "Characterization of distinct functional domains of transforming growth factor beta." Proc Natl Acad Sci U S A. Sep. 15, 1993; 90(18):8628-32.

Burmester et al., "Mutational analysis of a transforming growth factor-beta receptor binding site." Growth Factors. 1998;15(3):231-42.

Daopin et al., "Crystal structure of transforming growth factor-beta 2: an unusual fold for the superfamily." Science. Jul. 17, 1992; 257(5068):369-73.

Darlak et al., "Assessment of biological activity of synthetic fragments of transforming growth factor-alpha." J Cell Biochem. Apr. 1988; 36(4):341-52.

Hinck et al., "Transforming growth factor beta 1: three-dimensional structure in solution and comparison with the X-ray structure of transforming growth factor beta 2." Biochemistry. Jul. 2, 1996; 35(26):8517-34.

Huang et al., "A pentacosapeptide (CKS-25) homologous to retroviral envelope proteins possesses a transforming growth factor-beta activity." J Biol Chem. Feb. 27, 1998; 273(9):4815-8.

Huang et al., "Activated thyroglobulin possesses a transforming growth factor-beta activity." J Biol Chem. Oct. 2, 1998; 273(40):26036-41.

Huang et al., "Amyloid beta-peptide possesses a transforming growth factor-beta activity." J Biol Chem. Oct. 16, 1998; 273(42):27640-4.

Huang et al., "An active site of transforming growth factor-beta(1) for growth inhibition and stimulation." J Biol Chem. Sep. 24, 1999; 274(39):27754-8.

Huang et al., "Synthetic TGF-beta antagonist accelerates wound healing and reduces scarring." FASEB J. Aug. 2002; 16(10):1269-70. Epub Jun. 21, 2002.

Huang et al., "Transforming growth factor beta peptide antagonists and their conversion to partial agonists." J Biol Chem. Oct. 24, 1997; 272(43)27155-9.

(Continued)

*Primary Examiner*—David S Romeo
(74) *Attorney, Agent, or Firm*—Elmore Patent Law Group, P.C.; Carolyn S. Elmore

(57) ABSTRACT

This invention is drawn to methods of using peptide-based antagonists of TGF-beta to facilitate the healing of cutaneous wounds that includes burns, lacerations and scrapes. The administration of peptide TGF-beta antagonists to wounds results in reduced scarring, wound contraction and deposition of extracellular matrix components, and increased rates of re-epithelialization during wound healing.

4 Claims, 12 Drawing Sheets

OTHER PUBLICATIONS

Postlethwaite et al. "Identification of a chemotactic epitope in human transforming growth factor-beta 1 spanning amino acid residues 368-374." J Cell Physiol. Sep. 1995; 164(3):587-92.

Qian et al., "Binding affinity of transforming growth factor-beta for its type II receptor is determined by the C-terminal region of the molecule." J Biol Chem. Nov. 29, 1996; 271(48):30656-62.

Qian et al., "Characterization of mutated transforming growth factor-beta s which possess unique biological properties." Biochemistry. Oct. 11, 1994; 33(40):12298-304.

Qian et al., "Distinct functional domains of TGF-beta bind receptors on endothelial cells." Growth Factors. 1999; 17(1):63-73.

Qian et al., "Identification of a structural domain that distinguishes the actions of the type 1 and 2 isoforms of transforming growth factor beta on endothelial cells." Proc Natl Acad Sci U S A. Jul. 15, 1992; 89(14):6290-4.

Schlunegger and Grutter, "Refined crystal structure of human transforming growth factor beta 2 at 1.95 A resolution." J Mol Biol. May 20, 1993; 231(2):445-58.

Shah et al., "Neutralisation of TGF-beta 1 and TGF-beta 2 or exogenous addition of TGF-beta 3 to cutaneous rat wounds reduces scarring." J Cell Sci. Mar. 1995; 108 ( Pt 3):985-1002.

* cited by examiner

```
              1                                                   25
Human TGF-β1  A L D T N Y C F S S T E K N C C V R Q L Y I D F R
Human TGF-β2  A L D A A Y C F R N V Q D N C C L R P L Y I D F K
Human TGF-β3  A L D T N Y C F R N L E E N C C V R P L Y I D F R 26                                                  50
Human TGF-β1  K D L G W K W I H E P K G Y H A N F C L G P C P Y
Human TGF-β2  R D L G W K W I H E P K G Y N A N F C A G A C P Y
Human TGF-β3  Q D L G W K W V H E P K G Y Y A N F C S G P C P Y 51                                                  75
Human TGF-β1  I W S L D T Q Y S K V L A L Y N Q H N P G A S A A
Human TGF-β2  L W S S D T Q H S R V L S L Y N T I N P E A S A S
Human TGF-β3  L R S A D T T H S T V L G L Y N T L N P E A S A S 76                                                  100
Human TGF-β1  P C C V P Q A L E P L P I V Y Y V G R K P K V E Q
Human TGF-β2  P C C V S Q D L E P L T I L Y Y I G K T P K I E Q
Human TGF-β3  P C C V P Q D L E P L T I L Y Y V G R T P K V E Q 101           112
Human TGF-β1  L S N M I V R S C K C S    (SEQ ID NO. 1)
Human TGF-β2  L S N M I V K S C K C S    (SEQ ID NO. 2)
Human TGF-β3  L S N M V V K S C K C S    (SEQ ID NO. 3)
```

FIGURE 5A

```
β1²⁵ 41-65   ANFCLGPCPYIWSLDTQYSKVLALY   (SEQ ID NO. 4)
β2²⁵ 41-65   ANFCAGACPYLWSSDTQHSRVLSLY   (SEQ ID NO. 5)
β3²⁵ 41-65   ANFCSGPCPYLRSADTTHSTVLGLY   (SEQ ID NO. 6)
```

FIGURE 5B

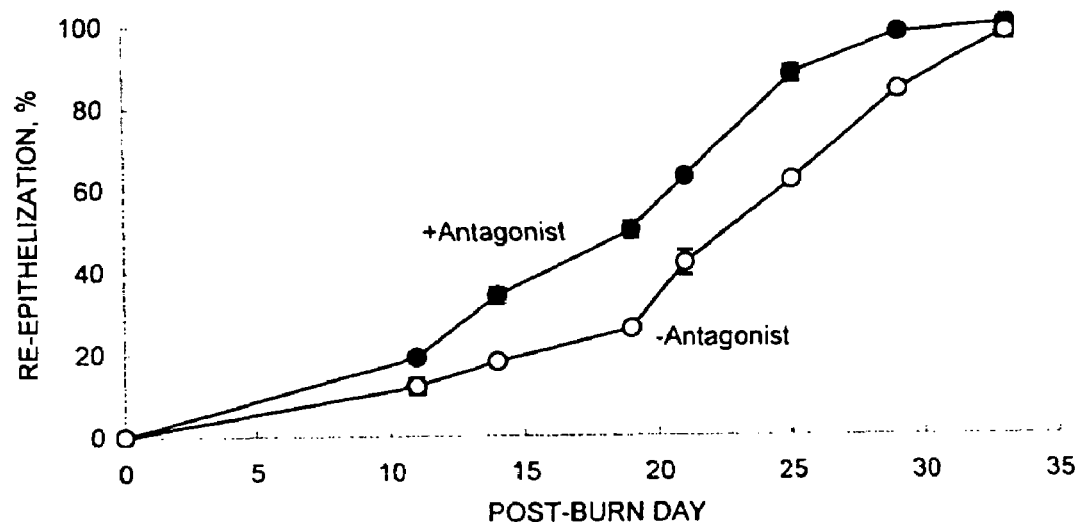
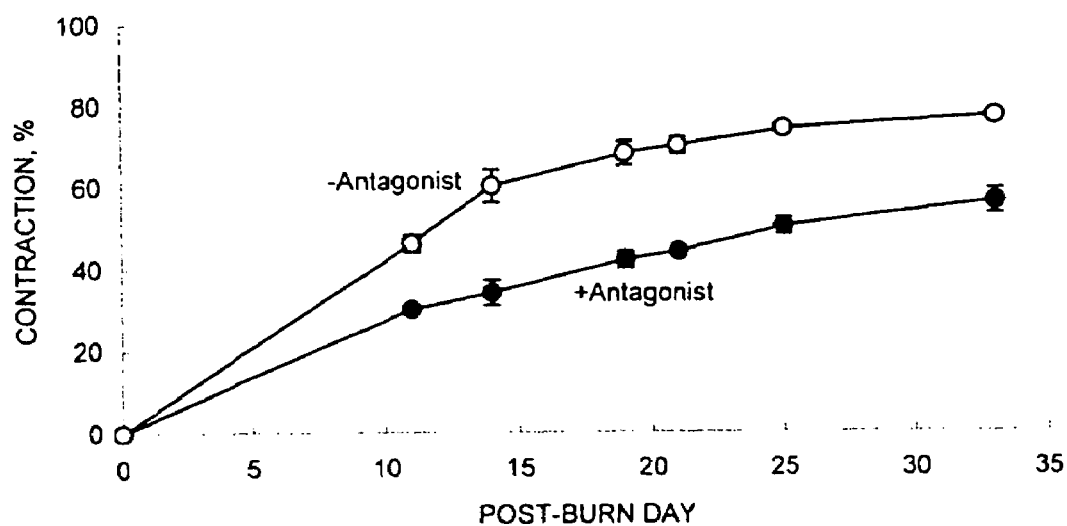
FIGURE 6

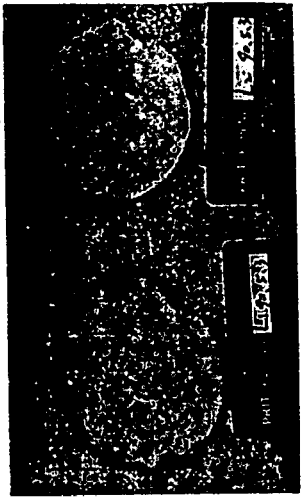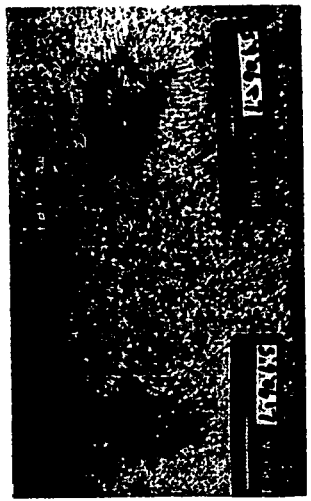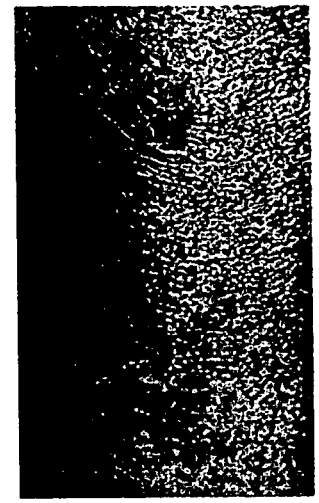
FIG. 7 Right
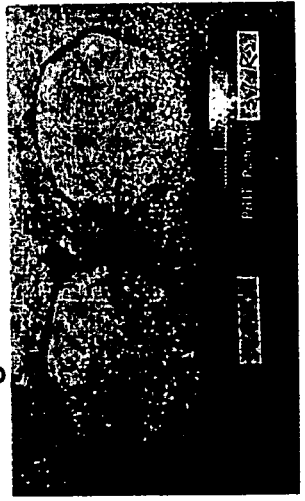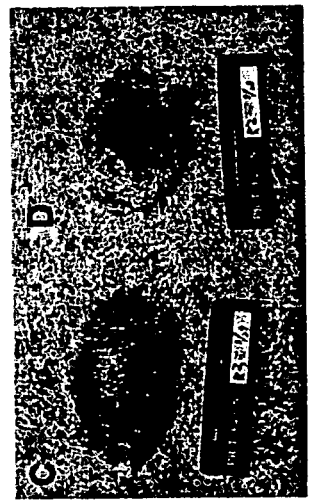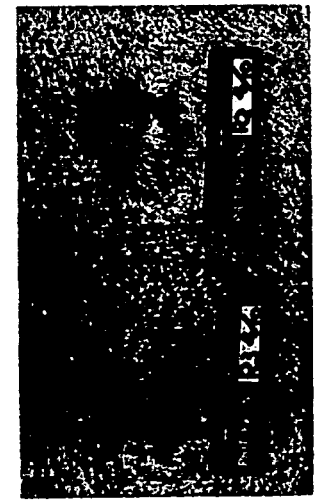
FIG. 7 Left

SEQUENCE LISTING

<160> NUMBER OF SEQ ID NOS: 14

<210> SEQ ID NO 1
<211> LENGTH: 112
<212> TYPE: PRT
<213> ORGANISM: Homo sapiens

<400> SEQUENCE: 1

```
Ala Leu Asp Thr Asn Tyr Cys Phe Ser Ser Thr Glu Lys Asn Cys Cys
 1               5                  10                  15
```

Val Arg Gln Leu Tyr Ile Asp Phe Arg Lys Asp Leu Gly Trp Lys Trp
            20                  25                  30

Ile His Glu Pro Lys Gly Tyr His Ala Asn Phe Cys Leu Gly Pro Cys
        35                  40                  45

Pro Tyr Ile Trp Ser Leu Asp Thr Gln Tyr Ser Lys Val Leu Ala Leu
    50                  55                  60

Tyr Asn Gln His Asn Pro Gly Ala Ser Ala Ala Pro Cys Cys Val Pro
65                  70                  75                  80

Gln Ala Leu Glu Pro Leu Pro Ile Val Tyr Tyr Val Gly Arg Lys Pro
                85                  90                  95

Lys Val Glu Gln Leu Ser Asn Met Ile Val Arg Ser Cys Lys Cys Ser
            100                 105                 110

<210> SEQ ID NO 2
<211> LENGTH: 112
<212> TYPE: PRT
<213> ORGANISM: Homo sapiens

<400> SEQUENCE: 2

Ala Leu Asp Ala Ala Tyr Cys Phe Arg Asn Val Gln Asp Asn Cys Cys
1               5                   10                  15

Leu Arg Pro Leu Tyr Ile Asp Phe Lys Arg Asp Leu Gly Trp Lys Trp
            20                  25                  30

Ile His Glu Pro Lys Gly Tyr Asn Ala Asn Phe Cys Ala Gly Ala Cys
        35                  40                  45

Pro Tyr Leu Trp Ser Ser Asp Thr Gln His Ser Arg Val Leu Ser Leu
    50                  55                  60

Tyr Asn Thr Ile Asn Pro Glu Ala Ser Ala Ser Pro Cys Cys Val Ser
65                  70                  75                  80

Gln Asp Leu Glu Pro Leu Thr Ile Leu Tyr Tyr Ile Gly Lys Thr Pro
                85                  90                  95

Lys Ile Glu Gln Leu Ser Asn Met Ile Val Lys Ser Cys Lys Cys Ser
            100                 105                 110

<210> SEQ ID NO 3
<211> LENGTH: 112
<212> TYPE: PRT
<213> ORGANISM: Homo sapiens

<400> SEQUENCE: 3

Ala Leu Asp Thr Asn Tyr Cys Phe Arg Asn Leu Glu Glu Asn Cys Cys
1               5                   10                  15

Val Arg Pro Leu Tyr Ile Asp Phe Arg Gln Asp Leu Gly Trp Lys Trp
            20                  25                  30

Val His Glu Pro Lys Gly Tyr Ala Asn Phe Cys Ser Gly Pro Cys
        35                  40                  45

Pro Tyr Leu Arg Ser Ala Asp Thr Thr His Ser Thr Val Leu Gly Leu
    50                  55                  60

Tyr Asn Thr Leu Asn Pro Glu Ala Ser Ala Ser Pro Cys Cys Val Pro
65                  70                  75                  80

Gln Asp Leu Glu Pro Leu Thr Ile Leu Tyr Tyr Val Gly Arg Thr Pro
                85                  90                  95

Lys Val Glu Gln Leu Ser Asn Met Val Val Lys Ser Cys Lys Cys Ser
            100                 105                 110

<210> SEQ ID NO 4
<211> LENGTH: 25

```
<212> TYPE: PRT
<213> ORGANISM: Homo sapiens

<400> SEQUENCE: 4

Ala Asn Phe Cys Leu Gly Pro Cys Pro Tyr Ile Trp Ser Leu Asp Thr
 1               5                  10                  15

Gln Tyr Ser Lys Val Leu Ala Leu Tyr
             20                  25

<210> SEQ ID NO 5
<211> LENGTH: 25
<212> TYPE: PRT
<213> ORGANISM: Human

<400> SEQUENCE: 5

Ala Asn Phe Cys Ala Gly Ala Cys Pro Tyr Leu Trp Ser Ser Asp Thr
 1               5                  10                  15

Gln His Ser Arg Val Leu Ser Leu Tyr
             20                  25

<210> SEQ ID NO 6
<211> LENGTH: 25
<212> TYPE: PRT
<213> ORGANISM: Homo sapiens

<400> SEQUENCE: 6

Ala Asn Phe Cys Ser Gly Pro Cys Pro Tyr Leu Arg Ser Ala Asp Thr
 1               5                  10                  15

Thr His Ser Thr Val Leu Gly Leu Tyr
             20                  25

<210> SEQ ID NO 7
<211> LENGTH: 10
<212> TYPE: PRT
<213> ORGANISM: Homo sapiens

<400> SEQUENCE: 7

Pro Tyr Ile Trp Ser Leu Asp Thr Gln Tyr
 1               5                  10

<210> SEQ ID NO 8
<211> LENGTH: 10
<212> TYPE: PRT
<213> ORGANISM: Homo sapiens

<400> SEQUENCE: 8

Pro Tyr Leu Trp Ser Ser Asp Thr Gln His
 1               5                  10

<210> SEQ ID NO 9
<211> LENGTH: 10
<212> TYPE: PRT
<213> ORGANISM: Homo sapiens

<400> SEQUENCE: 9

Pro Tyr Leu Arg Ser Ala Asp Thr Thr His
 1               5                  10

<210> SEQ ID NO 10
<211> LENGTH: 4
<212> TYPE: PRT
<213> ORGANISM: Homo sapiens
<220> FEATURE:
<221> NAME/KEY: PEPTIDE
```

```
<222> LOCATION: (1)..(4)
<223> OTHER INFORMATION: Residue 3 is any amino acid

<400> SEQUENCE: 10

Trp Ser Xaa Asp
 1

<210> SEQ ID NO 11
<211> LENGTH: 4
<212> TYPE: PRT
<213> ORGANISM: Homo sapiens
<220> FEATURE:
<221> NAME/KEY: PEPTIDE
<222> LOCATION: (1)..(4)
<223> OTHER INFORMATION: Residue 3 is any amino acid

<400> SEQUENCE: 11

Arg Ser Xaa Asp
 1

<210> SEQ ID NO 12
<211> LENGTH: 25
<212> TYPE: PRT
<213> ORGANISM: Homo sapiens

<400> SEQUENCE: 12

Ala Asn Phe Ser Leu Gly Pro Ser Pro Tyr Ile Trp Ser Leu Asp Thr
 1               5                  10                  15

Gln Tyr Ser Lys Val Leu Ala Leu Tyr
            20                  25

<210> SEQ ID NO 13
<211> LENGTH: 25
<212> TYPE: PRT
<213> ORGANISM: Human

<400> SEQUENCE: 13

Ala Asn Phe Ser Ala Gly Ala Ser Pro Tyr Leu Trp Ser Ser Asp Thr
 1               5                  10                  15

Gln His Ser Arg Val Leu Ser Leu Tyr
            20                  25

<210> SEQ ID NO 14
<211> LENGTH: 25
<212> TYPE: PRT
<213> ORGANISM: Homo sapiens

<400> SEQUENCE: 14

Ala Asn Phe Ser Ser Gly Pro Ser Pro Tyr Leu Arg Ser Ala Asp Thr
 1               5                  10                  15

Thr His Ser Thr Val Leu Gly Leu Tyr
            20                  25
```

PEPTIDE ANTAGONISTS OF TGF-BETA FAMILY MEMBERS AND THERAPEUTIC USES THEREOF

CROSS REFERENCE TO RELATED APPLICATIONS

This application is a continuation of U.S. patent application Ser. No. 10/135,946, filed Apr. 29, 2002 now abandoned, which is a continuation-in-part of U.S. patent application Ser. No. 09/095,637, filed on Jun. 11, 1998 now U.S. Pat. No. 6,500,920, which claims the benefit of priority to U.S. provisional application Ser. No. 60/050,202, now abandoned, which was filed on Jun. 19, 1997.

GOVERNMENTAL SUPPORT

This work was supported by the U.S. Department of Health and Human Services/National Institutes of Health grant number CA38808. The U.S. Government has certain rights in this invention.

SEQUENCE LISTING

A paper copy of the sequence listing and a computer readable form of the same sequence listing are appended below and herein incorporated by reference. The information recorded in computer readable form is identical to the written sequence listing, according to 37 C.F.R. 1.821 (f).

BACKGROUND OF THE INVENTION

1. Field of the Invention

The invention relates generally to antagonists of TGF-β activity, particularly to peptide antagonists of TGF-β activity. The invention also relates to methods of accelerating wound healing and preventing scarring by administering peptide antagonists of TGF-β activity to vertebrates.

2. Description of Related Art

Transforming growth factor β (TGF-β) is a family of 25-kDa structurally homologous dimeric proteins containing one interchain disulfide bond and four intrachain disulfide bonds. The TGF-β family is composed of three known members (TGF-$\beta_1$, TGF-$\beta_2$, and TGF-$\beta_3$) in mammalian species. TGF-β is a bifunctional growth regulator: it is a growth inhibitor for epithelial cells, endothelial cells, T-cells, and other cell types and a mitogen for mesenchymal cells. TGF-β also has other biological activities, including stimulation of collagen, fibronectin, and plasminogen activator inhibitor-1 (PAI-1) synthesis, stimulation of angiogenesis, and induction of differentiation in several cell lineages.

TGF-β has been implicated in the pathogenesis of various diseases such as cancer, macular degeneration, intimal hyperplasia following angioplasty, tissue fibrosis (which includes integument scar tissue formation, liver cirrhosis, kidney fibrosis, lung fibrosis, heart fibrosis and others) and glomerulonephritis. It is known in the art that TGF-β plays an important role in scarring of the skin or organ fibrosis, which occurs as a result of injury or other fibrogenic stimulus. TGF-β's role in wound healing and scarring revolves around its activity as an important regulator of the extracellular matrix stimulating fibroplasia and collagen deposition and inhibiting extracellular matrix degradation by up-regulating the syntheses of protease inhibitors (see Roberts, 1995; Roberts and Sporn, 1996; and O'Kane and Ferguson, 1997). Neutralizing antibodies to TGF-β have been used experimentally to reduce scarring of wounds, to prevent lung injury in adult respiratory distress syndrome (ARDS), and to block restenosis following angioplasty in animal models. These promising results warrant the development of TGF-β antagonists (inhibitor) that might be useful in inhibiting, ameliorating or reversing the effects of TGF-β and treating diseases. However, practical applications have been limited by the large molecular size of the antibodies with resulting instability and poor tissue penetration (O'Kane and Ferguson, ibid;, Shah et al., 1994; Shah et al., 1995).

TGF-β peptide antagonists that block TGF-β binding to cell surface receptors and inhibit TGF-β-induced growth and transcriptional activation are described in copending U.S. application Ser. No. 09/095,637 and Huang et al., *J. Biol. Chem.* 272:27155-27160 (1997). The effective concentrations ($EC_{50}$) of these peptide antagonists, with amino acid sequences corresponding to the 41st to 65th of TGF-$\beta_1$ and TGF-$\beta_2$, range from ~60 nM to 1 μM, depending on the targeted TGF-β isoform. In contrast to TGF-β neutralizing antibodies, the peptide antagonists are relatively stable, exert rapid inhibitory actions, and can be applied topically. These properties suggest that they are useful for treating hypertrophic scarring in cutaneous wounds.

3. Related Art Citations

Throughout the instant specification, numerical citations in parentheses are used to cite specific references. Those references appear below and are herein incorporated by reference. No admission to the status of these references as prior art are made.

1. Derynck, R., Jarrett, J. A., Chen, E. Y., Eaton, D. H., Bell, J. R., Assoian, R. K., Roberts, A. B., Sporn, M. B., and Goeddel, D. V. (1985) Nature 316, 701-705.
2. Laiho, M., Weis, F. M. B., and Massagué, J. (1990) J. Biol. Chem. 265:18518-18524.
3. Madison, L., Webb, N. R., Rose, T. M., Marquardt, H., Ikeda, T., Twardzik, D., Seyedin, S., and Purchio, A. F. (1988) DNA and Cell Biol. 7:18.
4. Schlunegger, M. P., and Grutter, M. G. (1992) Nature 353:430-434.
5. Hinck, A. P., Archer, S. J., Qian, S. W., Roberts, A. B., Sporn, M. B., Weatherbee, J. A., Tsang, M. L.-S., Lucas, R., Zhang, B.-L., Wenker, J., and Torchia, D. A. (1996) Biochem. 35:8517-8534.
6. Liu, Q., Huang, S. S., and Huang, J. S. (1997) J. Biol. Chem. 1997 272: 18891-18895.
7. O'Grady, P., Kuo, M.-D., Baldassare, J. J., Huang, S. S., and Huang, J. S. (1991) J. Biol. Chem. 288:8583-8589.
8. Roberts, A. B. (1995) Transforming growth factor-β: activity and efficacy in animal models of wound healing. Wound Rep. Reg. 3,408-418.
9. Roberts, A. B., and Sporn, M. B. (1996) Transforming growth factor-β. In: Clark, R. A. F., ed. The Molecular and Cellular Biology of Wound Repair, 2nd ed. New York, N.Y., Plenum Publishing Corp., 275-308.
10. O'Kane, S. and Ferguson, M. W. (1997) Transforming growth factor βs and wound healing. Internat. J. Biochem. Cell Biol. 29, 63-78.
11. Shah, M., Foreman, D. M., and Ferguson, M. W. J. (1994) Neutralising antibody to TGF-$\beta_{1,2}$ reduces cutaneous scarring in adult rodents. J. Cell Sci. 107, 1137-1157.
12. Shah, M., Foreman, D. M., and Ferguson, M. W. J. (1995) Neutralization of TGF-$\beta_1$ and TGF-$\beta_2$ or exogenous addition of TGF-$\beta_3$ to cutaneous rat wounds reduces scarring. J. Cell Sci. 108, 985-1002.
13. Huang, S. S., Liu, Q., Johnson, F. E., Konish, Y., and Huang, J. S. (1997) Transforming growth factor β peptide antagonists and their conversion to partial agonists. J. Biol. Chem. 272, 27155-27160.

14. Kaufman, t., Levin, M., and Hurwitz, D. J. (1984) The effect of topical hyperalimentation on wound healing rate and granulation tissue formation of experimental deep second degree burns in guinea pigs. Burns 10, 252-256.
15. Knabl, J. S., Bayer, G. S., Bauer, W. A., Schwendenwein, I., Dado, P. F., Kucher, C., Horvat, R., Turkof, E., Schossmann, B., and Meissl, G. (1999) Controlled partial skin thickness burns: an animal model for studies of burn wound progression. Burns 25, 229-235.
16. Kitamura, M., Shimizu, M., Ino, H., Okeie, K., Yamaguchi, M., Funjno, N., and Nakanishi, I. (2001) Collagen remodeling and cardiac dysfunction in patients with hypertrophic cardiomyopathy: the significance of type IV and VI collagens. Clin. Cardiol. 24, 325-329.
17. Winter, G. D. (1974) Histological aspects of burn wound healing. Burns 1, 191-196.
18. Mutoe, T. A., Pierce, G. F., Morishima, C., and Deuel, T. F. (1991) Growth factor-induced acceleration of tissue repair through direct and inductive activities in a rabbit dermal ulcer model. J. Clin. Invest. 87, 694-703.
19. Asheroft, G. S., Yang, X., Glick, A. B., Weinstein, M., Letterio, J. J., Mizel, D. E., Anzano, M., Greenwell-Wild, T., Wahl, S. M., Deng, C., and Roberts, A. B. (1999) Mice lacking Smad3 show accelerated wound healing and an impaired local inflammatory response. Nature Cell Biology 1,260-266.
20. Zambruno, G., Marchisio, P. C., Marconi, A., Vaschieri, C., Melchiori, A.; Giannetti, A., and DeLuca, M. (1995) Transforming growth factor-β modulates $β_1$ and $β_5$ integrin receptors and induces the de novo expression of the $αvβ_6$ heterodimer in normal human keratinocytes: implications for wound healing. J. Cell Biol. 129, 853-865.
21. Xia, Y.-P., Zhao, Y., Marcus, J., Jimenez, P. A., Ruben, S. M., Moore, P. A., Khan, F., and Mustoe, T. A. (1999) Effects of keratinocyte growth factor-2 (KGF-2) on wound healing in an ischemia-impaired rabbit ear model and on scar formation. J. Pathol. 188, 431-438.
22. Liu, Q., Ling. T.-Y., Shieh, H.-S., Johnson, F. E., Huang, J. S., and Huang, S. S. (2001) Identification of the high affinity binding site in transforming growth factor-β involved in complex formation with $α_2$-macroglobulin: Implications regarding the molecular mechanisms of complex formation between $α_2$-macroglobulin and growth factors, cytokines and hormones. J. Biol. Chem. 276, 46212-46218.

SUMMARY OF THE INVENTION

The inventor has discovered that specific peptide-based TGF-β antagonists are effective in accelerating wound healing and reducing scarring due to wounds, such as burns, scrapes, puncture wounds and lacerations. The TGF-β antagonist peptides may comprise any one of amino acid sequences as set forth in SEQ ID NO:4-11. The advantages to using the TGF-β antagonist peptides in the treatment of skin wounds and diseases mediated by TGF-β activity are the chemical stability of the peptides, ease of manufacturing the peptides, and small size of the peptides, which allows for rapid penetration into the wound relative to anti-TGF-β antibodies.

The invention is drawn to a non-naturally occurring peptide that comprises an amino acid sequence derived from TGF-β1, TGF-β2 or TGF-β3, wherein the peptide is capable of binding to a TGF-β receptor, thereby rendering the TGF-β receptor unavailable for the binding of TGF-β molecules. The peptide comprises a core stretch of amino acids as set forth in SEQ ID NO:10 or SEQ ID NO:11. The preferred peptide comprises an amino acid sequence according to SEQ ID NO:4, SEQ ID NO:5, SEQ ID NO:6, SEQ ID NO:7, SEQ ID NO:8 or SEQ ID NO:9. The peptide may also comprise an amino acid sequence that is at least 68% identical to any one of SEQ ID NO:4, SEQ ID NO:5 and SEQ ID NO:6.

The invention is also drawn to methods of treating diseases in a vertebrate that are mediated by TGF-β or TGF-β receptor activity, comprising the step of administering to the vertebrate a peptide that is a TGF-β antagonist. Diseases that are mediated by TGF-β or TGF-β receptor activity include cancer (via reduced immune function or increased angiogenesis), morbid angiogenesis (which includes e.g., macular degeneration and tumor growth), intimal hyperplasia, cancer, scarring, fibrosis (e.g., liver cirrhosis, kidney fibrosis lung fibrosis, cystic fibrosis, heart fibrosis), diseases of reduced immune function, glomerulonephritis, and respiratory distress syndrome. The peptide comprises a core stretch of amino acids as set forth in SEQ ID NO:10 or SEQ ID NO:11. The preferred peptide comprises an amino acid sequence according to SEQ ID NO:4, SEQ ID NO:5, SEQ ID NO:6, SEQ ID NO:7, SEQ ID NO:8 or SEQ ID NO:9. The peptide may also comprise an amino acid sequence that is at least 68% identical to any one of SEQ ID NO:4, SEQ ID NO:5 and SEQ ID NO:6.

The invention is also drawn to methods of inhibiting the activity of TGF-β in a vertebrate, comprising the step of administering to the vertebrate a peptide that is a TGF-β antagonist. "Inhibiting the activity of TGF-β" means inhibiting, ameliorating or reversing the physiological effects mediated by TGF-β in biological systems. Those physiological effects include scar formation, deposition of collagen or other extracellular matrix proteins during wound healing, wound contraction, inhibition or slowing of re-epithelialization (the proliferation of epithelial cells, usually epidermal cells) during the process of healing, restenosis of a blood vessel after angioplasty and the development of some types of cancers. The peptide comprises a core stretch of amino acids as set forth in SEQ ID NO:10 or SEQ ID NO:11. The preferred peptide comprises an amino acid sequence according to SEQ ID NO:4, SEQ ID NO:5, SEQ ID NO:6, SEQ ID NO:7, SEQ ID NO:8 or SEQ ID NO:9. The peptide may also comprise an amino acid sequence that is at least 68% identical to any one of SEQ ID NO:4, SEQ ID NO:5 and SEQ ID NO:6.

The invention is further drawn to methods of treating wounds comprising the step of topically administering to a wound a composition comprising a vehicle and a peptide that is a TGF-β antagonist. The method of wound treatment may have any of the following outcomes, which are relative to wounds that have not been treated with the composition: the reduction of scarring, the reduction of wound contraction, the reduction of the deposition of extracellular matrix components, such as adhesion proteins (fibronectin, laminin, and vitronectin are examples of adhesion proteins) and collagens (collagens are of several types, including type I, type II, type III, type IV, type V, type VI and type IX collagen), and the promotion of re-epithelialization during wound healing. The peptide comprises a core stretch of amino acids as set forth in SEQ ID NO:10 or SEQ ID NO:11. The preferred peptide comprises an amino acid sequence according to SEQ ID NO:4, SEQ ID NO:5, SEQ ID NO:6, SEQ ID NO:7, SEQ ID NO:8 or SEQ ID NO:9. The peptide may also comprise an amino acid sequence that is at least 68% identical to any one of SEQ ID NO:4, SEQ ID NO:5 and SEQ ID NO:6. A preferred vehicle comprises a physiological buffer, such as phosphate buffered saline and a gel, which contains a modified carboxymethyl-cellulose polymer and propylene glycol, such as IntraSite® Gel Hydrogel Wound Dressing (Smith & Nephew, plc, London UK). Wounds include puncture wounds, pressure wounds, abrasions, lacerations and burns. Wounds may be in any vertebrate, including humans.

The invention is further drawn to pharmaceutical compositions comprising a peptide that is a TGF-β antagonist in a pharmaceutically acceptable excipient.

BRIEF DESCRIPTION OF THE DRAWINGS

FIG. 5: Panel A shows the amino acid sequences of three TGF-β molecules and Panel B shows three peptides derived from the TGF-β molecules, extending from amino acid residue number 41 to 65.

FIG. 6: Kinetics of re-epithelialization and contraction in pig burn wounds treated with a TGF-β peptantagonist peptide TGF-beta antagonist). The rates of wound re-epithelization and contraction were measured as a percent of the original wound (panels A and B, respectively). The burns treated with the TGF-β peptantagonist (peptide TGF-beta antagonist) healed faster than the control wounds after post-burn day 10 (p<0.005). The burns treated with the TGF-β peptantagonist (peptide TGF-beta antagonist) contracted significantly after post-burn day 10 when compared with the control treated with vehicle only (p<0.005).

FIG. 7: Acceleration of wound healing and reduction of scarring by application of a TGF-β peptantagonist (peptide TGF-beta antagonist) to burn wounds of pigs. Burn wounds treated with a TGF-β peptantagonist (peptide TGF-beta antagonist) or vehicle (gel without peptide) only in two animals (left and right) were photographed immediately after burn injury (left, panel A and B and right, panel A and B), post-burn day 23 (left, panel C and D), post-burn day 34 (right, panel C and D), post-burn day 35 (left, panel E and F) and post-burn day 41 (right, panel E and F). After burn injury, necrosis was present (white color) (left and right, panel A and B). The control wounds exhibited a large open wound on post-burn day 23 (left, panel D). In contrast, the wound treated with the TGF-β peptantagonist (peptide TGF-beta antagonist) showed very little open wound (left, panel C). On post-burn day 35 and 41, less scar formation was observed in the wound treated with a TGF-β peptantagonist (peptide TGF-beta antagonist) when compared with the control wound (left, panel E versus left, panel F and right, panel F versus panel E, respectively).

DETAILED DESCRIPTION OF THE INVENTION

Figure 1:
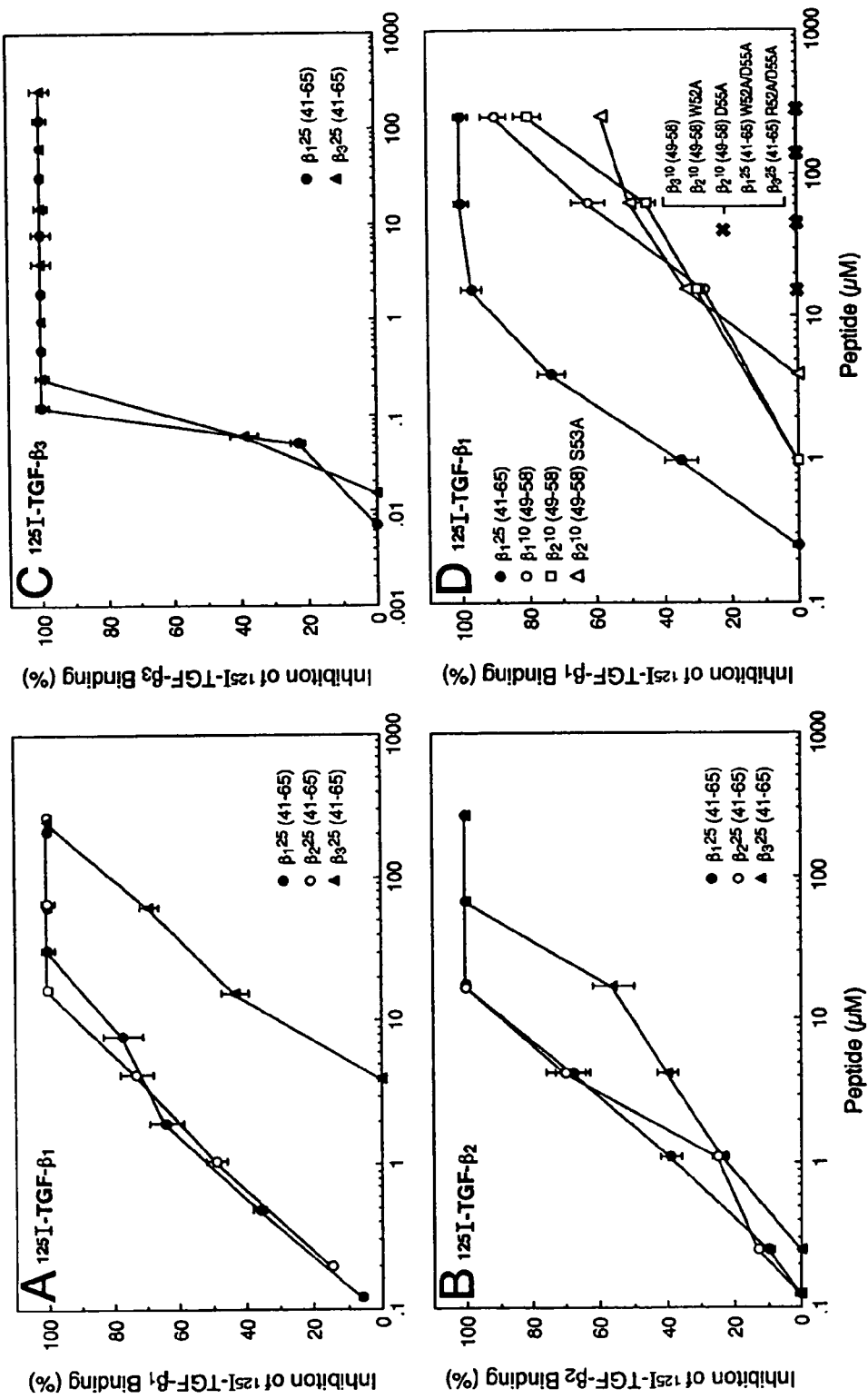
FIG. 1: Effect of various concentrations of pentacosapeptides, decapeptides, and their structural variants on TGF-β binding to TGF-β receptors in mink lung epithelial cells. Cells were incubated with $^{125}$I-TGF-$β_1$, (Panels A and D), $^{125}$I-TGF-$β_2$ (Panel B), and $^{125}$I-TGF-$β_3$ (Panel C) both with and without 100-fold excess of unlabeled TGF-β isoforms and various concentrations of peptides $β_1^{25}$ (41-65), $β_2^{25}$ (41-65), and $β_3^{25}$ (41-65) (Panels A, B, and C) or of $β_1^{10}$ (49-58), $β_2^{10}$ (49-58), $β_3^{10}$ (49-58), $β_1^{10}$ (49-58) W52A, $β_2^{10}$ (49-58) S53A, $β_2^{10}$ (49-58) D55A, $β_1^{25}$ (41-65) W52A/D55A and $β_3^{25}$ (41-65) R52A/D55A (Panel D). The specific binding of $^{125}$I-labeled TGF-$β_1$ isoforms was then determined. The specific binding obtained in the absence of peptide antagonists was taken as 0% inhibition. The specific binding (0% inhibition) of $^{125}$I-TGFβ$_1$, $^{125}$I-TGFβ$_2$, and $^{125}$I-TGFβ$_3$, were 3930±540 cpm/well, 4512±131 cpm/well, and 4219±125 cpm/well, respectively. The error bars are means±S.D. of triplicate cultures.

TGF-β antagonists or inhibitors that specifically bind to TGF-β receptors, which include type I, type II, type III and type V receptors, are disclosed. It was discovered that three chemically synthesized peptides, which correspond in sequence to amino acid numbers 41-65 of TGF-$β_1$ (SEQ ID NO:4), TGF-$β_2$ (SEQ ID NO:5), and TGF-$β_3$ (SEQ ID NO:6), and which comprise a core amino acid sequence as set forth in SEQ ID NO:10 or SEQ ID NO:11, inhibit the binding of TGF-$β_1$, TGF-$β_2$, and TGF-$β_3$, to TGF-β receptors in epithelial cells. The peptides also block TGF-β-induced growth inhibition and TGF-β-induced expression of PAI-1 in epithelial cells. It was also discovered that the W/RXXD motif found within the peptide sequences determines the specificity of activity of the antagonist peptide. In view of these discoveries, peptides that comprise amino acid sequences corresponding to SEQ ID NO:10 or SEQ ID NO:11 are considered to be antagonists of TGF-β activity. It was also discovered that these TGF-β peptide antagonists can be converted to partial agonists (i.e., agent which mimics the effects of TGF-β) by conjugation to carriers such as proteins or synthetic polymers.

A stepwise sequence comparison between SEQ ID NO:4 (amino acids 41-65 of TGF-β1), SEQ ID NO:5 (amino acids 41-65 of TGF-β2), and SEQ ID NO:6 (amino acids 41-65 of TGF-β3), has revealed that SEQ ID NO:4 and SEQ ID NO:6 are 68% identical; SEQ ID NO:4 and SEQ ID NO:5 are 80% identical; and SEQ ID NO:5 and SEQ ID NO:6 are 72% identical. Thus non-naturally occurring TGF-β peptide agonists may comprise an amino acid sequence that is at least 68% identical to any one of SEQ ID NO:4, SEQ ID NO:5, and SEQ ID NO:6; and including the decapeptides of SEQ ID NO:7, SEQ ID NO:8, and SEQ ID NO:9.

Percent identity is intended to mean the percentage of the same amino acid residues between two sequences. To determine the percent identity of any given peptide, the reference sequence may be SEQ ID NO:4, SEQ ID NO:5 or SEQ ID NO:6. The two sequences being compared are aligned using the Clustal method (Higgins et al, *Cabios* 8:189-191, 1992) of multiple sequence alignment in the Lasergene biocomputing software (DNASTAR, INC, Madison, Wis.). In this method, multiple alignments are carried out in a progressive manner, in which larger and larger alignment groups are assembled using similarity scores calculated from a series of pairwise alignments. Optimal sequence alignments are obtained by finding the maximum alignment score, which is the average of all scores between the separate amino acid residues in the alignment, determined from a residue weight table representing the probability of a given amino acid change occurring in two related peptides over a given evolutionary interval. Penalties for opening and lengthening gaps in the alignment contribute to the score. The default parameters used with this program are as follows: gap penalty for multiple alignment=10; gap length penalty for multiple alignment=10; k-tuple value in pairwise alignment=1; gap penalty in pairwise alignment=3; window value in pairwise alignment=5; diagonals saved in pairwise alignment=5. The residue weight table used for the alignment program is PAM250 (Dayhoff et al., in *Atlas of Protein Sequence and Structure*, Dayhoff, Ed., NBRF, Washington, Vol. 5, suppl. 3, p. 345, 1978).

The invention is thus drawn to non-naturally occurring peptides, and modifications thereof, that antagonize TGF-β activity, and compositions comprising peptides that antagonize of TGF-β activity. By "non-naturally occurring", it is meant that the peptide is artificially produced by chemical synthesis, genetic recombinant methods or enzymatic digestion of isolated polypeptides, and that the peptide does not comprise a full length mature TGF-β polypeptide. The non-naturally occurring peptide may be modified, wherein such modifications include glycosylation, lipidation, amidation, phosphorylation, acetylation, PEGylation (the addition of polyethylene glycol to stabilize the peptide) and albumination (the conjugation of an albumin moiety to increase the biological half-life of the peptide). By "antagonize", it is meant that the non-naturally occurring peptide of the instant invention binds to a TGF-β receptor and prevents the activation of that TGF-β receptor. Antagonization may be complete or it may be partial, whereby some TGF-β receptor activation may occur in the vertebrate after administration of the non-naturally occurring peptide. As used herein, "TGF-β receptors" are integral membrane proteins that bind TGF-β molecules. TGF-β receptors generally comprise a type I receptor component and a type II receptor component. Presently, there are seven known mammalian members of type I receptors, including activin receptor-like kinases 1 to 6 (ALK1-ALK6), and five known members of type II receptors, including activin type II and type IIB receptor (ActRII/IIB), TGF-β type II receptor (TβRII), BMP type II receptor (BMPRII), and MIS type II receptor (MISRII). TGF-β receptors, in addition to type I and type II types, also include type III and type V receptors (Ref. 6). However, in the practice of this invention, yet to be identified TGF-β receptors are covered by the term "TGF-β receptor". For a brief review of TGF-β receptor biology, see Moustakas, et al., *J. Cell Sci.* 114:4359-4369, which is herein incorporated by reference.

The non-naturally occurring peptides bind to TGF-β receptors, thereby blocking the binding of active TGF-β receptor agonists to TGF-β receptors and "inhibiting the activity of TGF-β". The activities of TGF-β, mimetics of TGF-β or TGF-β receptor agonists, which are well known in the art, include (a) both proliferation and anti-proliferation effects on certain cells and tissues, depending on the state and type of cell, (b) cell differentiation, cell death, cell migration, embryonic development, tumor growth and wound healing, and (c)

promoting the production of cell-adhesion molecules, extracellular matrix molecules and other growth factors. For a review on TGF-β structure and function, see Lodish et al., "Molecular Cell Biology," Third Edition, Scientific American Books (1995), Gilbert, Scott F., "Developmental Biology," Fifth Edition, Sinauer Associates, Inc., (1997), and Alberts et al., "Molecular Biology of the Cell," Third Edition, Garland Publishing, Inc. (1994), which are herein incorporated by reference.

The non-naturally occurring peptide TGF-β antagonists of the present invention are useful in treating individuals suffering from diseases or conditions that are modulated at least in part by TGF-β. Diseases and conditions which may be ameliorated by the administration of peptide TGF-β antagonists include carcinomas, such as breast cancer and pancreatic cancer (see Gold, L. I., [1999] "The role of transforming growth factor-β (TGF-β) in human cancer", *Crit. Rev. Oncol.* 10:303-360; which is herein incorporated by reference), developmental defects, such as neural tube defects, wounds, such as cutaneous burns, lacerations, punctures and abrasions, intimal hyperplasia (which results in blood vessel blockage by the thickening of arterial lining) and restenosis of blood vessels after angioplasty, angiogenesis that allows tumor growth, insufficient immune system function, angiogenesis (which is involved in e.g., tumor growth and macular degeneration), tumor metastasis (through the activity of proteases on the extracellular matrix), fibrosis (e.g., integument scarring, cystic fibrosis, liver cirrhosis, kidney fibrosis, lung fibrosis, and heart fibrosis) glomerulonephritis, and respiratory distress syndrome. The invention is therefore also drawn to therapeutic or pharmaceutical compositions, which comprise a peptide TGF-β antagonist, useful in the treatment of diseases or conditions that are modulated at least in part by TGF-β.

It has been discovered by the inventor that a peptide TGF-β antagonist, which comprises a sequence of SEQ ID NO:10 or SEQ ID NO:11, (a) accelerates re-epithelialization of skin and reduces wound contraction and scarring during the healing of a burn injury and diminishes wound contraction and scarring, relative to untreated control wounds, in both the pig and rabbit excision injury models. "Re-epithelialization" is the growth of the outer layer of skin or epidermis over the wound during the healing process. "Hypertrophic scarring", "scarring", or "fibrosis" is the process whereby fibrous connective tissue replaces dermis or any other connective tissue that lies subjacent to an epithelium during tissue repair. "Wound contraction" is the process whereby scar tissue or granulation tissue contracts. The discovery that re-epithelialization is accelerated by a peptide TGF-β antagonist was surprising and unexpected. Burn wound healing consists of epithelialization, contraction and formation of granulation and scar tissue (Refs. 8-12). TGF-β is believed to be involved in most of these events. The peptide TGF-β antagonist of the present invention is thought to block or slow down the occurrence of these events. However, the data shown in the examples that follow are consistent with a report that Smad3-null mice have accelerated cutaneous wound healing compared with wild-type mice (Ref. 18). Wounds in these animals have an increased rate of re-epithelialization and significantly reduced local infiltration of monocytes. The Smad3 signaling plays an important role in TGF-β-stimulated expression of collagen, chemotaxis of monocytes and growth inhibition of keratinocytes. The mechanism of enhanced re-epithelialization in wounds treated with the peptide TGF-β antagonist of the present invention may involve increased keratinocyte proliferation (transient inhibition of keratinocyte proliferation by TGF-β may be an integral component in the complex process of wound healing) coupled with a migration response stimulated by growth factors other than TGF-β (Refs. 18-21). The peptide TGF-β antagonist of the present invention has been shown to block complex formation between $\alpha_2$-macroglobulin and growth factors, cytokines and hormones (see reference 15) and thus, may enhance activation of these substances or agents by blocking inhibition of their activities mediated by α2-macroglobulin.

Peptide TGF-β antagonists of the present invention comprise the amino acid motif W/RSXD, wherein X is any amino acid (SEQ ID NO:10 and SEQ ID NO:11). The W/RXXD motif was demonstrated to be an important site involved in the interaction of peptides with TGF-β receptors. This conclusion is supported by several lines of evidence presented in Examples, including: 1) among the seven pentacosapeptides (peptides consisting of 25 amino acids), whose amino acid sequences cover most of the TGF-$β_1$ molecule, only peptide $β_1^{25}$ (41-65), which contains the W/RXXD motif in the middle of the peptide amino acid sequence, has TGF-β antagonist activity; 2) pentacosapeptides and decapeptides (peptides consisting of 10 amino acids) containing this W/RXXD motif are potent TGF-β antagonists; 3) replacement of W-52/R-52 and D-55 by alanine residues abolishes the antagonist activities of these decapeptides and pentacosapeptides; 4) conjugation of the peptide $β_1^{25}$ (41-65) antagonist to carrier proteins creates a partial TGF-β agonist; and 5) several proteins that possess W/RXXD motifs have TGF-β agonist and antagonist activities. Preferred peptide TGF-β antagonists comprise any one of SEQ ID NO:4, SEQ ID NO:5, SEQ ID NO:6, SEQ ID NO:7, SEQ ID NO:8 or SEQ ID NO:9; or peptides that are at least 68% identical to these sequences.

The therapeutic or pharmaceutical compositions of the present invention may be administered by any suitable route known in the art including for example via intraarterial catheterization, intravenous, subcutaneous, intramuscular, transdermal, intrathecal, intracerebral, oral or topical. Administration may be either rapid as by injection or over a period of time as by slow infusion or administration of slow release formulation. For treating tissues in the central nervous system, administration may be by injection or infusion into the cerebrospinal fluid (CSF). When it is intended that a peptide TGF-β antagonist be administered to cells in the central nervous system, administration may be with one or more agents capable of promoting penetration of a peptide TGF-β antagonist across the blood-brain barrier. For treating intimal hyperplasia or restenosis, the peptide antagonist may be administered via intraarterial catheterization during angioplasty procedures. The peptide may also be applied on the surface of the stent that is left in place during angioplasty. When it is intended that the peptide TGF-β antagonist be used to reduce scar tissue (fibrosis) formation during the healing of surgical incisions, especially incisions made during plastic surgery procedures, the peptide TGF-β antagonist peptide may be subcutaneously injected into the area of the incision or healing wound.

A peptide TGF-β antagonist may also be linked or conjugated with agents that provide desirable pharmaceutical or pharmacodynamic properties. For example, a peptide TGF-β antagonist may be coupled to any substance known in the art to promote penetration or transport across the blood-brain barrier such as an antibody to the transferrin receptor, and administered by intravenous injection. (See for example, Friden et al., *Science* 259:373-377, 1993 which is incorporated by reference). Furthermore, a peptide TGF-β antagonist may be stably linked to a polymer such as polyethylene glycol or albumin to obtain desirable properties of solubility, stability, half-life and other pharmaceutically advantageous properties. (See for example Davis et al. *Enzyme Eng* 4:169-73, 1978; Burnham, *Am J Hosp Pharm* 51:210-218, 1994 which are incorporated by reference).

The compositions comprising peptide TGF-β antagonists are usually employed in the form of pharmaceutical preparations. Such preparations are made in a manner well known in the pharmaceutical art. One preferred preparation utilizes a vehicle of physiological saline solution, but it is contemplated that other pharmaceutically acceptable carriers such as physiological concentrations of other non-toxic salts, five percent aqueous glucose solution, sterile water or the like may also be used. It may also be desirable that a suitable buffer be present in the composition. Such solutions may, if desired, be lyophilized and stored in a sterile ampoule ready for reconstitution by the addition of sterile water for ready injection. The primary solvent may be aqueous or alternatively non-aqueous. A peptide TGF-β antagonist may also be incorporated into a solid or semi-solid biologically compatible matrix which may be implanted into tissues requiring treatment. A peptide TGF-β antagonist may also be incorporated into a hydrogel wound dressing, such as an IntraSite® Gel Hydrogel Wound Dressing (Smith & Nephew, plc, London UK), which comprises a modified carboxymethyl-cellulose polymer and propylene glycol.

The carrier may also contain other pharmaceutically-acceptable excipients for modifying or maintaining the pH, osmolarity, viscosity, clarity, color, sterility, stability, rate of dissolution, or odor of the formulation. Similarly, the carrier may contain still other pharmaceutically-acceptable excipients for modifying or maintaining release or absorption or penetration across membranes or other barriers, such as the epidermis, the lining of the alimentary canal, the endothelium or the blood-brain barrier.

It is also contemplated that certain formulations containing a peptide TGF-β antagonist are to be administered orally. Such formulations are preferably encapsulated and formulated with suitable carriers in solid dosage forms. Some examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, gelatin, syrup, methyl cellulose, methyl- and propylhydroxybenzoates, talc, magnesium, stearate, water, mineral oil, and the like. The formulations may additionally include lubricating agents, wetting agents, emulsifying and suspending agents, preserving agents, sweetening agents or flavoring agents. The compositions may be formulated so as to provide rapid, sustained, or delayed release of the active ingredients after administration to the patient by employing procedures well known in the art. The formulations may also contain substances that diminish proteolytic degradation and promote absorption such as, for example, surface active agents.

The specific dose is calculated according to the approximate body weight or body surface area of the patient or the volume of body space to be occupied. The dose will also be calculated dependent upon the particular route of administration selected. Further refinement of the calculations necessary to determine the appropriate dosage for treatment is routinely made by those of ordinary skill in the art. Such calculations may be made without undue experimentation by one skilled in the art in light of the activity of a peptide TGF-β antagonist. The data showing activity of a peptide TGF-β antagonist are herein disclosed in the Examples and in copending application Ser. No. 09/095,637, which is herein incorporated by reference. Furthermore, the activity of a peptide TGF-β antagonist on a particular target cell type may be determined by routine experimentation. Exact dosages are determined in conjunction with standard dose-response studies. It will be understood that the amount of the composition actually administered will be determined by a practitioner, in the light of the relevant circumstances including the condition or conditions to be treated, the choice of composition to be administered, the age, weight, and response of the individual patient, the severity of the patient's symptoms, and the chosen route of administration.

The above disclosure describes several preferred embodiments of the invention. The skilled artisan will recognize that other embodiments of this invention, which are not overtly disclosed herein, may be employed in the practice of this invention. The invention is further illustrated by the examples described below, which are not meant to limit the invention.

EXAMPLES

Example 1

Development of Peptide Antagonists of TGF-β
Experimental Procedures

Materials. $Na^{125}$ (17 Ci/mg) and [methyl-$^3$H]thymidine (67 Ci/mmole) were purchased from ICN Radiochemicals (Irvine, Calif.). High molecular-weight protein standards (myosin, 205 kDa; β-galactosidase, 116 kDa; phosphorylase, 97 kDa; bovine serum albumin, 66 kDa), chloramine T, bovine serum albumin (BSA), and human carbonic anhydrase I (CA) were purchased from Sigma Company (St. Louis, Mo.). Disuccinimidyl suberate (DSS) was obtained from Pierce (Rockford, Ill.). TGF-$β_1$ was purchased from Austral Biologicals (San Ramon, Calif.). TGF-$β_2$ and TGF-$β_3$ were purchased from R&D Systems (Minneapolis, Minn.).

Preparation of peptides. The amino acid sequences of all peptides were derived from those of TGF-$β_1$, TGF-$β_2$, and TGF-$β_3$. For peptides $β_1^{25}$ (41-65), $β_2^{25}$ (41-65), and $β_3^{25}$ (41-65), other versions in which cysteine-44 and cysteine-48 were replaced by serine residues were also synthesized. These C44S/C48S versions of peptides $β_1^{25}$ (41-65) (SEQ ID NO:4), $β_2^{25}$ (41-65) (SEQ ID NO:5), and $β_3^{25}$ (41-65) (SEQ ID NO:6) had the same TGF-β antagonist activity. The C44S/C48S version of peptide $β_1^{25}$ (41-65) is designated SEQ ID NO:12, the C44S/C48S version of the peptide $β_2^{25}$ (41-65) is designated SEQ ID NO: 13, and the C44S/C48S version of peptide of $β_3^{25}$ (41-65) is designated SEQ ID NO:14. The C44S/C48S versions had better stability in solution during storage, so they were used in most of the experiments. The peptides were synthesized using tert-butoxycarbonyl chemistry on an Applied Biosystems Model 431A peptide synthesizer and purified using Sephadex G-25 column chromatography and reverse-phase HPLC (C-8 column). The purity of the synthesized peptides were verified by automated Edman degradation on an Applied Biosystems Model 477A gas/liquid phase protein sequenator with an on-line Applied Biosystems Model 120A phenylthiohydantoin amino acid analyzer. The purity of all peptides was estimated to be ≧95%.

Preparation of peptide $β_1^{25}$ (41-65)-carbonic anhydrase (CA) and peptide $β_1^{25}$ (41-65)-bovine serum albumin (BSA) conjugates. 150 μl of 3 mM peptide $β_1^{25}$ (41-65) (SEQ ID NO:4) in phosphate buffer saline (pH adjusted to ~9.0) was mixed with 300 μl of 0.1 M $NaHCO_3$ (pH ~9.0) containing BSA or CA (0.5 mg) and 10 μl of 27 mM DSS in dimethyl sulfoxide. After 18 hr at 4° C., the reaction mixture was mixed with 50 μl of 1 M ethanolamine HCl in 0.1 M $NaHCO_3$ (~pH 9.0). After 2 hr at room temperature, the reaction mixture was dialyzed against 2 liters of 0.1 M $NaHCO_3$ (~pH 9.0). After four changes of the dialysis solution, the sample was stored at 4° C. prior to use. The molar ratio of peptide $\beta_1^{25}$ (41-65)/carrier protein in the conjugate was determined by amino acid composition analysis.

Specific binding of $^{125}$I-labeled TGF-$\beta_1$, TGF-$\beta_2$, and TGF-$\beta_3$ ($^{125}$I-TGF-$\beta_1$, $^{125}$I-TGF-$\beta_2$, and $^{125}$I-TGF-$\beta_3$) to TGF-$\beta$ receptors in mink lung epithelial cells. $^{125}$I-TGF-$\beta_1$, $^{125}$I-TGF-$\beta_2$, and $^{125}$I-TGF-$\beta_3$ were prepared by iodination of TGF-$\beta_1$, TGF-$\beta_2$, and TGF-$\beta_3$ with Na$^{125}$I as described previously (Ref. 7). The specific radioactivities of $^{125}$I-TGF-$\beta_1$, $^{125}$I-TGF-$\beta_2$, and $^{125}$I-TGF-$\beta_3$ were 1-3×10$^5$ cpm/ng. Mink lung epithelial cells were grown on 24-well clustered dishes to near confluence in Dulbecco's modified Eagle medium (DMEM) containing 10% fetal calf serum. The epithelial cells were incubated with 0.1 nM $^{125}$I-TGF-$\beta_1$, $^{125}$I-TGF-$\beta_2$, or $^{125}$I-TGF-$\beta_3$ both with and without 100-fold excess of unlabeled TGF-$\beta_1$, TGF-$\beta_2$, or TGF-$\beta_3$ in binding buffer (Ref. 7). After 2.5 hr at 0° C., the cells were washed two times with binding buffer, and the cell-associated radioactivity was determined. The specific binding of $^{125}$I-labeled TGF-$\beta$ isoforms to TGF-$\beta$ receptors in the cells was calculated by subtracting non-specific binding (in the presence of 100-fold excess of the unlabeled TGF-$\beta$ isoforms) from total binding. All experiments were carried out in triplicate cell cultures.

$^{125}$I-TGF-$\beta_1$-affinity labeling of cell-surface TGF-$\beta$ receptors in mink lung epithelial cells. Mink lung epithelial cells grown on 60-mm Petri dishes were incubated with 0.1 nM $^{125}$I in the presence of various concentrations of peptide $\beta_1^{25}$ (41-65) or peptide $\beta_3^{25}$ (41-65) in binding buffer. After 2.5 hr at 0° C., $^{125}$I-TGF-$\beta_1$-affinity labeling was carried out in the presence of DSS as described. The $^{125}$I-TGF-$\beta_1$-affinity-labeled TGF-$\beta$ receptors were analyzed by 5% SDS-polyacrylamide gel electrophoresis under reducing conditions and autoradiography.

[Methyl-$^3$H]thymidine Incorporation—Mink lung epithelial cells grown on 24-well clustered dishes were incubated with various concentrations of TGF-$\beta_1$ in the presence and absence of peptide $\beta_1^{25}$ (41-65) or with various concentrations of peptide $\beta_1^{25}$ (41-65)-CA, and peptide $\beta_1^{25}$ (41-65)-BSA in DMEM containing 0.1% fetal calf serum. After 16 hr at 37° C., the cells were pulsed with 1 μCi/ml of [methyl-$^3$H]thymidine for 4 hr. The cells were then washed twice with 1 ml of 10% trichloroacetic acid and once with 0.5 ml of ethanol:ether (2:1, v/v). The cells were then dissolved in 0.4 ml of 0.2 N NaOH and counted with a liquid scintillation counter.

RNA Analysis—Mink lung epithelial cells were grown overnight in 12-well clustered dishes in DMEM containing 10% fetal calf serum. The medium was then changed to DMEM containing 0.1% fetal calf serum and the cells were incubated with 0.25 and 2.5 pM TGF-$\beta_1$ in the presence of various concentrations of peptide $\beta_1^{25}$ (41-65) for 2.5 hr. Total cellular RNA was extracted using RNAzol B (Tel-Test Inc.) according to the manufacturer's protocol. RNA was electrophoresed in 1.2% agarose-formaldehyde gel and transferred to Duralon-UV membranes using 10×SSC. The membranes were probed at 42° C. with a random-primed, radiolabeled 1-kb fragment from the Hind III and NeoI digests of PAI-1 cDNA and glyceraldehyde-3-phosphate dehydrogenase ("GAPDH") cDNA. The blots were washed with 0.1× SSC containing 0.1% SDS at room temperature.

Experimental Results

To develop peptide antagonists of TGF-$\beta$, seven pentacosapeptides (peptides containing 25 amino acids) were synthesized: peptide $\beta_1^{25}$ (21-45), peptide $\beta_1^{25}$ (31-55), peptide $\beta_1^{25}$ (41-65) (SEQ ID NO:4), peptide $\beta_1^{25}$ (51-75), peptide $\beta_1^{25}$ (61-85), peptide $\beta_1^{25}$ (71-95), and peptide $\beta_1^{25}$ (81-105), whose amino acid sequences overlap one another and cover most of the human TGF-$\beta_1$ molecule, the monomer of which has 112 amino acid residues (SEQ ID NO:1) (ref. 1). The antagonist activities of these peptides were first tested for their abilities to inhibit $^{125}$I-labeled TGF-$\beta_1$ ($^{125}$I-TGF-$\beta_1$) binding to cell-surface TGF-$\beta$ receptors in mink lung epithelial cells, an art recognized model system for investigating TGF-$\beta$ receptor types and TGF-$\beta$-induced cellular responses (ref. 2). Peptide $\beta_1^{25}$ (41-65) (SEQ ID NO:4), completely inhibited the $^{125}$I-TGF-$\beta_1$ binding (specific binding without peptides=3672±524 cpm/well) to TGF-$\beta$ receptors in mink lung epithelial cells at 34 μM. The other six pentacosapeptides did not show any effect on $^{125}$I-TGF-$\beta_1$ binding to TGF-$\beta$ receptors in these epithelial cells, even at a concentration of 136 μM. This demonstrates that peptide $\beta_1^{25}$ (41-65) (SEQ ID NO:4) is a TGF-$\beta$ inhibitor or antagonist.

TGF-$\beta$ isoforms (TGF-$\beta_1$, TGF-$\beta_2$, and TGF-$\beta_3$) have been shown to exhibit different potencies in inducing cellular responses in certain cell types or systems. There is ~70% amino acid sequence homology at the 41st to 65th amino acid residues among these three TGF-$\beta$ isoforms (Refs. 1-3) (FIG. 5A). To determine the potencies of peptide $\beta_1^{25}$ (41-65) (SEQ ID NO:4), peptide $\beta_2^{25}$ (41-65) (SEQ ID NO:5), and peptide $\beta_3^{25}$ (41-65) (SEQ ID NO:6) in terms of TGF-$\beta$ antagonist activity, the effects of these peptides on the binding of $^{125}$I-labeled TGF-$\beta_1$, TGF-$\beta_2$, and TGF-$\beta_3$ to TGF-$\beta$ receptors in mink lung epithelial cells were measured. As shown in FIG. 1, both peptide $\beta_1^{25}$ (41-65) and peptide $\beta_2^{25}$ (41-65) inhibited $^{125}$I-TGF-$\beta_1$ and $^{125}$I-TGF-$\beta_2$ binding to TGF-$\beta$ receptors in a concentration-dependent manner with an IC$_{50}$ of ~1-2 μM (FIG. 1, A and B). Peptide $\beta_3^{25}$ (41-65) was weaker with an IC$_{50}$ of ~20 μM for inhibiting $^{125}$I-TGF-$\beta_1$ and $^{125}$I-TGF-$\beta_2$ binding to TGF-$\beta$ receptors (FIG. 1, A and B). In contrast, peptides $\beta_1^{25}$ (41-65) and $\beta_3^{25}$ (41-65) showed equal potency (IC$_{50}$=~0.06-0.08 μM) when $^{125}$I-TGF-$\beta_3$ was used as ligand for testing the inhibitory activity (FIG. 1, C). Peptide $\beta_2^{25}$ (41-65) also had an IC$_{50}$ of ~0.08 μM for inhibiting $^{125}$I-TGF-$\beta_3$ binding to TGF-$\beta$ receptors in these epithelial cells. These results show that both peptides $\beta_1^{25}$ (41-65) and $\beta_2^{25}$ (41-65) are more potent antagonists than peptide $\beta_3^{25}$ (41-65) for $^{125}$I-TGF-$\beta_3$ and $^{125}$I-TGF-$\beta_2$, and that all three pentacosapeptides are potent antagonists for $^{125}$I-TGF-$\beta_3$ with equal IC$_{50}$.

The region spanning residues 41-65 comprises a loop in the three-dimensional structure of TGF-$\beta_1$ and TGF-$\beta_2$ (Ref. 4, 5). This loop is accessible to solvent according to X-ray and NMR analyses (Ref. 4, 5). There are two reasons why a WSXD (for TGF-$\beta_1$ and TGF-$\beta_2$; SEQ ID NO:10) or RSXD (for TGF-$\beta_3$ SEQ ID NO:11) motif in the loop is a good candidate site whereby these antagonist peptides and their parent molecules could interact with TGF-$\beta$ receptors. The W/RSXD (52$^{nd}$-55$^{th}$ amino acid residues) motif is located on the exposed surface of the loop, and the side chains of the amino acid residues in the motif orient toward the solvent (Ref. 4, 5). Also, this motif may determine the affinities of peptides $\beta_1^{25}$ (41-65), $\beta_2^{25}$ (41-65), and $\beta_3^{25}$ (41-65), and their parent molecules for binding to TGF-$\beta$ receptors. Both peptide $\beta_1^{25}$ (41-65) and peptide $\beta_2^{25}$ (41-65) share the same motif (WSXD; SEQ ID NO:10) and have equal potencies (IC$_{50}$=~1-2 μM) for the inhibition of $^{125}$I-TGF-$\beta_1$ binding to TGF-$\beta$ receptors. Peptide $\beta_3^{25}$ (41-65) possesses a distinct motif of RSXD (SEQ ID NO:11) and is a weaker inhibitor (IC$_{50}$ of ~20 μM). The K$_d$s for TGF-$\beta_1$ and TGF-$\beta_2$ binding to the type V TGF-$\beta$ receptor are identical (~0.4 nM), whereas the Kd of TGF-$\beta_3$ binding to the type V receptor is higher (~5 nM) (Ref. 6).

To test the possibility that the W/RSXD motif is the active site of these peptides, three decapeptides designated $\beta_1^{10}$ (49-58), $\beta_2^{10}$ (49-58), and $\beta_3^{10}$ (49-58), which respectively correspond to SEQ ID NO:7, SEQ ID NO:8 and SEQ ID NO:9, were designed. The W/RSXD variants of these decapeptides, in which the W-52, S-53, or D-55 residue was replaced by an alanine residue, were also synthesized and designated peptide $\beta_2^{10}$ (49-58) W52A, peptide $\beta_2^{10}$ (49-58) S53A, and peptide $\beta_2^{10}$ (49-58) D55A, respectively. The ability of each of these decapeptides to inhibit $^{125}$I-TGF-$\beta_1$ binding to TGF-$\beta$ receptors in mink lung epithelial cells were then examined. As shown in FIG. 1D, both peptide $\beta_1^{10}$ (49-58) and peptide $\beta_2^{10}$ (49-58) inhibited the $^{125}$I-TGF-$\beta_1$ binding to TGF-$\beta$ receptors in a concentration-dependent manner with an IC$_{50}$ of ~40-70 µM. Peptide $\beta_3^{10}$ (49-58) did not show any inhibitory activity at concentrations up to ~300 µM. Peptide $\beta_2^{10}$ (49-58) S53A was equipotent with an IC$_{50}$ of ~40 µM. The other variants, peptide $\beta_2^{10}$ (49-58) W52A and peptide $\beta_2^{10}$ (49-58) D55A, failed to inhibit $^{125}$I-TGF-$\beta_1$ binding to TGF-$\beta$ receptors in these epithelial cells. Identical experiments with peptides $\beta_1^{10}$ (49-58) W52A, $\beta_1^{10}$ (49-58) S53A, and $\beta_1^{10}$ (49-58) D55A were also carried out, and the results were similar to those shown in FIG. 2D with the $\beta_2^{10}$ (49-58) peptide variants. These results suggest that the WXXD motif is important for the inhibitory activity of the decapeptides $\beta_1^{10}$ (49-58) and $\beta_2^{10}$ (49-58).

To demonstrate that the W/RYXD motif is also important for the inhibitory activities of the pentacosapeptides $\beta_1^{25}$ (41-65) and $\beta_3^{25}$ (41-65), variants of peptides $\beta_1^{25}$ (41-65) and $\beta_3^{25}$ (41-65), in which both W- or R-52 and D-55 were replaced by alanine residues, were prepared. These peptide variants were designated $\beta_1^{25}$ (41-65) W52A/D55A and $\beta_3^{25}$ (41-65) R52A/D55A, respectively, and tested for their inhibitory activities. FIG. 1D shows that peptide $\beta_1^{25}$ (41-65) W52A/D55A and peptide $\beta_3^{25}$ (41-65) R52A/D55A did not inhibit $^{125}$I-TGF-$\beta_1$ binding to TGF-$\beta$ receptors, thereby supporting the conclusion that the motif W/RXXD is involved in the interactions of the instant peptide antagonists with TGF-$\beta$ receptors.

Figure 2:
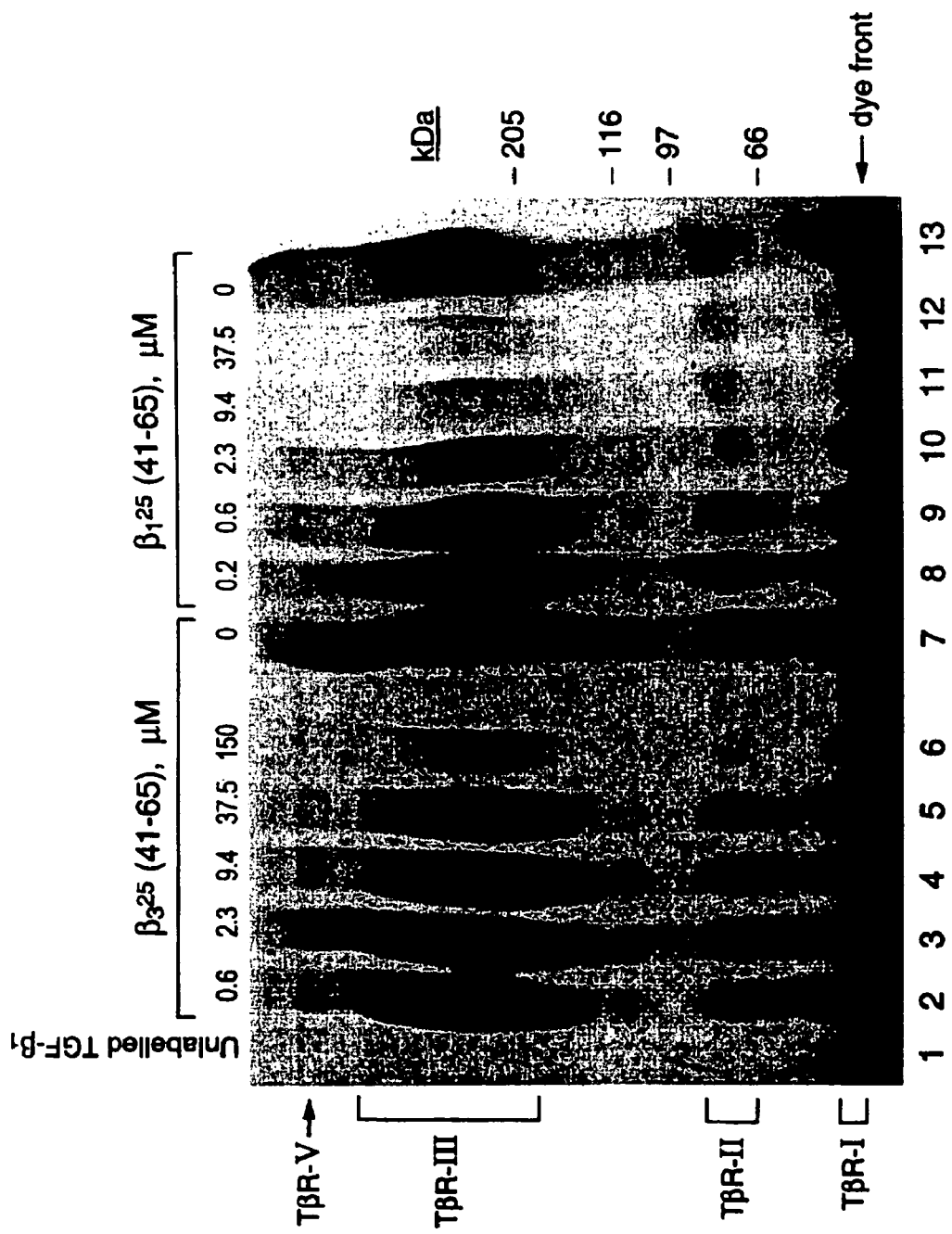
FIG. 2: $^{125}$I-TGF-$β_1$-affinity labeling of cell-surface TGF-β receptors after incubation of mink lung epithelial cells with $^{125}$I-TGFβ$_1$ in the presence of various concentrations of peptides $β_1^{25}$ (41-65) and $β_3^{25}$ (41-65). Cells were incubated with $^{125}$I-TGF-$β_1$ in the presence of 100-fold excess of unlabeled TGF-$β_1$ (lane 1) and of various concentrations of $β_1^{25}$ (41-65) (lanes 8-13) and $β_3^{25}$ (41-65) (lanes 2-7). The $^{125}$I-TGF-$β_1$ affinity labeling was carried out in the presence of DSS. The $^{125}$I-TGF-$β_1$ affinity-labeled TGF-β receptors were analyzed by 5% SDS-polyacrylamide gel electrophoresis and autoradiography. The arrow indicates the location of the $^{125}$I-TGF-$β_1$ affinity-labeled type V TGF-β receptor (TβR-V). The brackets indicate the locations of the $^{125}$I-TGF-$β_1$ affinity-labeled type I, type II, and type III TGF-β receptors (TβR-I, TβR-II, and TPR-III).

Mink lung epithelial cells express all of the known TGF-$\beta$ receptors (type I, type II, type III, and type V receptors) (see Ref. 6). To determine the relative sensitivities of TGF-$\beta$ receptor types to inhibition by peptides $\beta_1^{25}$ (41-65) and $\beta_3^{25}$ (41-65) with respect to ligand binding, mink lung epithelial cell-surface TGF-$\beta$ receptors were labeled with $^{125}$I-TGF-$\beta_1$ in the presence of various concentrations of peptides $\beta_1^{25}$ (41-65) and $\beta_3^{25}$ (41-65). As shown in FIG. 2, all cell-surface TGF-$\beta$ receptors (type I, type II, type III, and type V receptors) were affinity-labeled with $^{125}$I-TGF-$\beta_1$ in the absence of the antagonists (lanes 7 and 13). Peptide $\beta_1^{25}$ (41-65) appeared to inhibit the $^{125}$I-TGF-$\beta_1$-affinity labeling of all TGF-$\beta$ receptor types in a concentration-dependent manner (lanes 8-12). However, $\beta_1^{25}$ (41-65) inhibition of the $^{125}$I-TGF-$\beta_1$-affinity labeling of the type V TGF-$\beta$ receptor was greater than its inhibition of other TGF-$\beta$ receptor types. The $^{125}$I-TGF-$\beta_1$-affinity labeling of the type V TGF-$\beta$ receptor was almost completely abolished by peptide $\beta_1^{25}$ (41-65) at 2.3 µM, whereas the $^{125}$I-TGF-$\beta_1$-affinity labeling of other TGF-$\beta$ receptor types was only partially inhibited (30-40%) (FIG. 2, lane 10). This result is consistent with the observation that the affinity for TGF-$\beta_1$ binding to the type V TGF-$\beta$ receptor is ~20-40-fold lower than those for TGF-$\beta_1$ binding to other TGF-$\beta$ receptor types (Ref. 6). Peptide $\beta_3^{25}$ (41-65) showed weak activity in blocking the $^{125}$I-TGF-$\beta_1$-affinity labeling of the type V TGF-$\beta$ receptor (FIG. 2, lanes 2-5).

Figure 3:
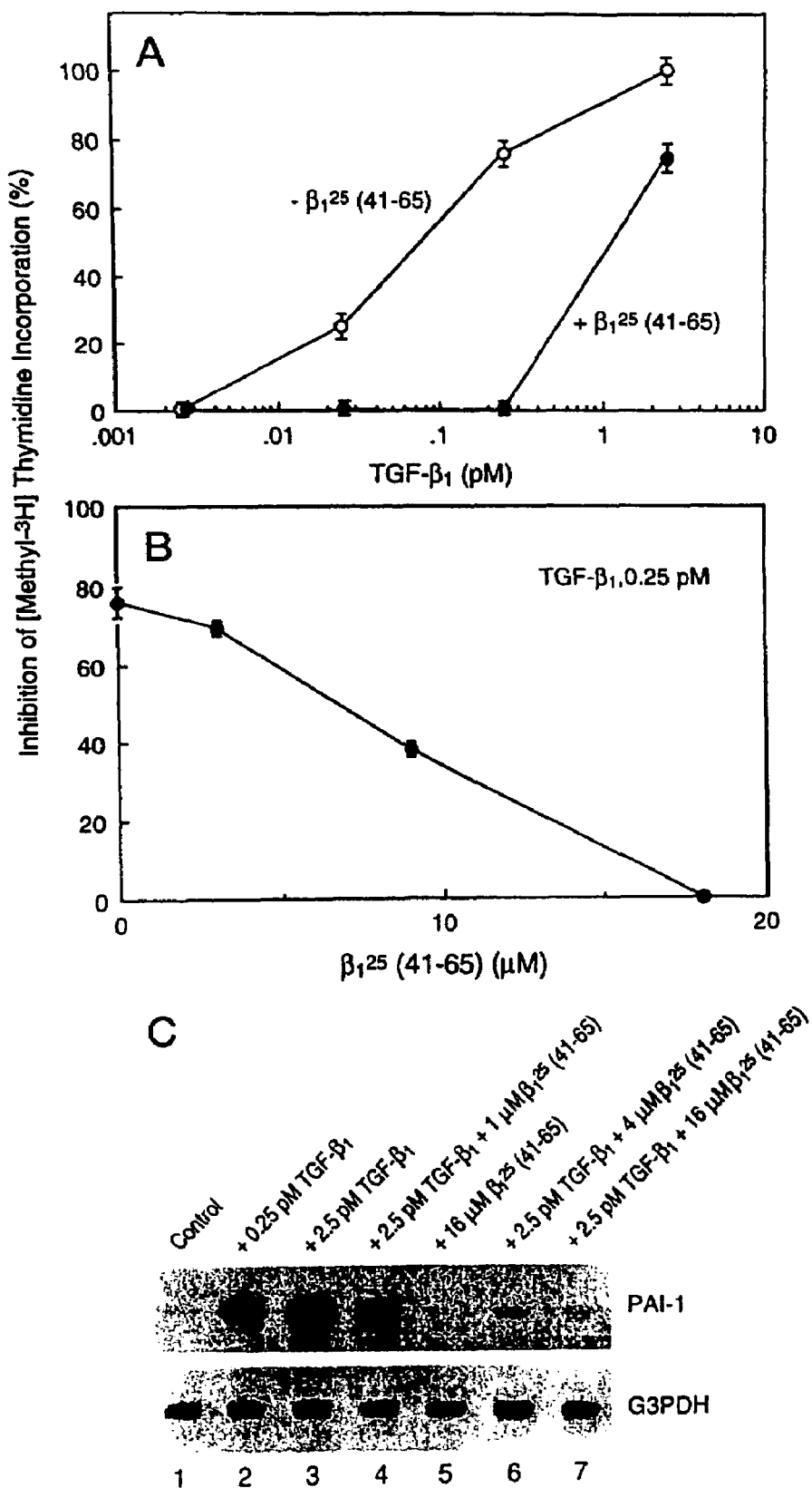
FIG. 3: Effect of peptide $β_1^{25}$ (41-65) on TGF-$β_1$ induced growth inhibition as measured by DNA synthesis, and TGF-$β_1$, induced PAI-1 expression in mink lung epithelial cells. (Panel A) Cells were incubated with various concentrations of TGF-$β_1$ in the presence of 18 μM peptide $β_1^{25}$ (41-65). [Methyl-$^3$H]thymidine incorporation into cellular DNA was then determined. The [methyl-$^3$H]thymidine incorporation into cellular DNA in cells treated with and without 10 pM TGF-$β_1$, were taken as 100 and 0% inhibition. The error bars are means±S.D. of triplicate cultures. (Panel B) Cells were incubated with 0.25 pM TGF-$β_1$ in the presence of various concentrations of peptide $β_1^{25}$ (41-65). The [methyl-$^3$H]thymidine incorporation into cellular DNA in cells treated with and without 10 pM TGF-$β_1$ were taken as 100 and 0% inhibition, respectively. The error bars are means±S.D. of triplicate cultures. (Panel C) Cells were treated with 0.25 and 2.5 pM TGF-$β_1$ and various concentrations of peptide $β_1^{25}$ (41-65) for 3 hr. The transcriptional expressions of PAI-1 and glyceraldehyde-3-phosphate dehydrogenase (G3PDH) were determined by Northern blot analysis.

It has been demonstrated that peptides $\beta_1^{25}$ (41-65), $\beta_2^{25}$ (41-65), and $\beta_3^{25}$ (41-65) are potent inhibitors for $^{125}$I-TGF-$\beta_1$ binding to TGF-$\beta$ receptors. To further establish the role of the instant peptides as TGF-$\beta$ antagonists or inhibitors, these peptides are shown to block a TGF-$\beta$-induced cellular response, i.e., growth inhibition. The effect of peptide $\beta_1^{25}$ (41-65) on TGF-$\beta_1$-induced growth inhibition was investigated by exposing mink lung epithelial cells to various concentrations of TGF-$\beta_1$ in the presence of 18 µM peptide $\beta_1^{25}$ (41-65) and measuring cellular DNA synthesis. As shown in FIG. 3A, DNA synthesis inhibition induced by 0.025 pM and 0.25 pM TGF-$\beta_1$ was completely blocked by peptide $\beta_1^{25}$ (41-65). In the presence of peptide $\beta_1^{25}$ (41-65), the dose-response curve of TGF-$\beta_1$ shifted to the right. Peptide $\beta_1^{25}$ (41-65) blocked TGF-$\beta_1$-induced growth inhibition in a concentration-dependent manner (FIG. 3B). It is important to note that peptide $\beta_1^{25}$ (41-65) (0.1 µM to 36 µM) did not have an effect on DNA synthesis in the absence of TGF-$\beta_1$. These results suggest that peptide $\beta_1^{25}$ (41-65) is a TGF-$\beta$ antagonist, which blocks TGF-$\beta$-induced growth inhibition.

The other prominent biological activity of TGF-$\beta$ is transcriptional activation of collagen, adhesion protein (i.e., fibronectin), and PAI-1. To see if peptide $\beta_1^{25}$ (41-65) is able to block this activity, the effect of peptide $\beta_1^{25}$ (41-65) on PAI-1 expression in mink lung epithelial cells stimulated by 0.25 pM and 2.5 pM TGF-$\beta_1$ was investigated. As shown in FIG. 3C, peptide $\beta_1^{25}$ (41-65) completely blocked the PAI-1 expression stimulated by TGF-$\beta_1$ (lane 7 versus lanes 3 and 5). These results further support the conclusion that peptide $\beta_1^{25}$ (41-65) is a potent TGF-$\beta$ antagonist.

Figure 4:
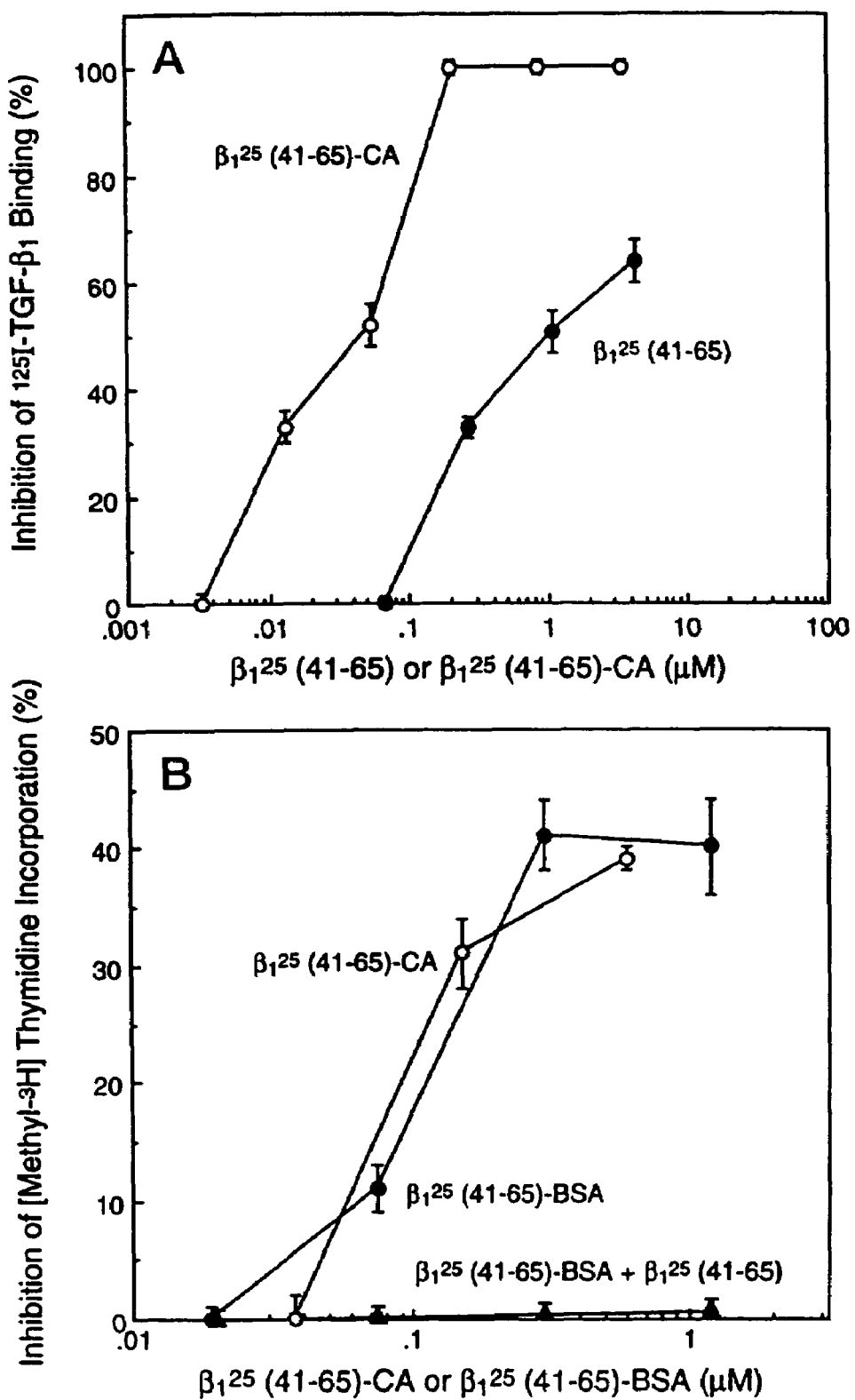
FIG. 4: Effect of $β_1^{25}$ (41-65)-CA and $β_1^{25}$ (41-65)-BSA peptide conjugates on $^{125}$I-TGF-$β_1$ binding to TGF-β receptors in mink lung epithelial cells and on mink lung epithelial cell growth as measured by DNA synthesis. (Panel A) Cells were incubated with $^{125}$I-TGF-$β_1$ in the presence and absence of 100-fold excess of unlabeled TGF-$β_1$ and various concentrations of $β_1^{25}$ (41-65)-CA peptide conjugate. The specific binding of $^{125}$I-TGF-$β_1$ was then determined. The specific binding of $^{125}$I-TGF-$β_1$ obtained in the absence of the conjugates was taken as 0% inhibition. The error bars are means±S.D. of triplicate cultures. (Panel B) Cells were treated with various concentrations of $β_1^{25}$ (41-65)-CA or $β_1^{25}$ (41-65)-BSA peptide conjugate. [Methyl-$^3$H]thymidine incorporation into cellular DNA was determined. The [methyl-$^3$H]thymidine incorporation into cellular DNA in cell treated with and without 10 pM TGF-$β_1$ were taken as 100 and 0% inhibition, respectively. The error bars are means±S.D. of triplicate cultures.

The dimeric structure of TGF-$\beta$ has been shown to be required for its biological activities. The hetero-oligomerization of TGF-$\beta$ receptors induced by the TGF-$\beta$ dimer appears to trigger signaling. If peptide $\beta_1^{25}$ (41-65) contains the active site sequence involved in the interaction of TGF-$\beta_1$ with TGF-$\beta$ receptors, one may be able to convert its antagonist activity to agonist activity by conjugating peptide $\beta_1^{25}$ (41-65) to carrier proteins, such that the $\beta_1^{25}$ (41-65)-protein conjugates would carry multiple valences of the putative active site. To test this possibility, peptide $\beta_1^{25}$ (41-65) was conjugated to carrier proteins CA (carbonic anhydrase) and BSA (bovine serum albumin) using the cross-linking agent DSS. DSS mainly cross-links the $\alpha$-amino group of peptide $\beta_1^{25}$ (41-65) to the C-amino groups of the carrier proteins. The $\beta_1^{25}$ (41-65)-BSA and $\beta_1^{25}$ (41-65)-CA conjugates contained ~5-10 molecules of peptide $\beta_1^{25}$ (41-65) per molecule of carrier protein. As shown in FIG. 4A, the $\beta_1^{25}$ (41-65)-CA conjugate inhibited $^{125}$I-TGF-$\beta_1$ binding to TGF-$\beta$ receptors in mink lung epithelial cells with an IC$_{50}$ of ~0.05 µM. The $\beta_1^{25}$ (41-65)-BSA conjugate had a similar IC$_{50}$ of ~~0.06 1M. These IC$_{50}$ are ~20-fold lower than that of peptide $\beta_1^{25}$ (41-65) prior to conjugation. In the control experiments, both BSA and CA conjugated without peptides did not have inhibitory activity. These results demonstrate that the multiple valences of the active site in the protein conjugates enhance its affinity for binding to TGF-$\beta$ receptors.

Potential agonist activities of the $\beta_1^{25}$ (41-65)-protein conjugates was also examined. As shown in FIG. 4B, both $\beta_1^{25}$ (41-65)-CA and $\beta_1^{25}$ (41-65)-BSA conjugates induced a small but significant growth inhibition as measured by DNA synthesis with an ED$_{50}$ of ~0.1 µM, although neither showed significant effects on the expression of PAI-1 in mink lung epithelial cells (data not shown). The growth inhibition (~30-40%) induced by 0.2 µM $\beta_1^{25}$ (41-65)-CA could be abolished in the presence of 10 μM $\beta_1{}^{25}$ (41-65) (data not shown). These results suggest that these $\beta_1{}^{25}$ (41-65)-protein conjugates are partial TGF-β agonists.

Example 2

Peptide TGF-β Antagonist Reduces Scarring and Promotes Healing Experimental Procedures Materials—Peptide $\beta_1{}^{25}$ (41-65) (SEQ ID NO:4) was synthesized and purified as described previously (Ref. 13). Sterile IntraSite® gel was obtained from Smith and Nephew Medical, Limited (England). Ketamine was obtained from Yung-Shin Pharmaceutical Co. (Taoyuan, Taiwan). Strenil® (azaperonum) and atropine were purchased from Janssen Animal Health BVBA, Belgium and China Chemical and Pharmaceutical Co. (Taipei, Taiwan), respectively. Monoclonal antibodies to type I collagen and fibronectin were purchased from Sigma (St. Louis, Mo.).

Animals—Female pigs (yorkshire strain and house inbred) weighing 20-25 kg and six rabbits weighing 3 kg were used. The pigs were housed in individual rooms, whereas female rabbits were kept in individual cages. Animals were fed standard laboratory chow and water ad libitum. All study protocols were reviewed and approved by the respective institutional animal care committees.

Preparation of IntraSite® gel containing TGF-β peptantagonist (peptide TGF-beta antagonist). 1 ml of sterile 6 mM peptide $\beta_1{}^{25}$ (41-65) in phosphate buffered saline or 1 ml of sterile phosphate buffered saline was vigorously mixed with 3 ml of IntraSite® gel using two 10 ml syringes connected with a three-way connector. The Intrasite® gel containing peptide $\beta_1{}^{25}$ (41-65) and Intrasite® gel containing buffer without peptide were stable at least for several weeks. The concentrations of peptide $\beta_1{}^{25}$ (41-65) (0.75 and 1.5 mM) were found to be effective in accelerating wound healing and reducing scarring under the experimental conditions. However, 1.5 mM of peptide $\beta_1{}^{25}$ (41-65) was used throughout the experiments described below.

Burn wound model. Four pigs weighing 20-25 kg were anesthetized by intramuscular injection of ketamine (5 mg/kg), strenil® (cazaporonum) (20 mg/kg) and atropine (5 mg/kg). Six uniform burn wounds (110° C., 30 sec) were then made symmetrically on the back of each pig using a modified soldering iron (Ref. 15) with a flat contact area of 20 cm². The burn injury was equivalent to a full-thickness burn injury in humans and uniformly caused coagulation and necrosis of dermis. After wounding, a thin layer of Intrasite®) gel containing either peptide $\beta_1{}^{25}$ (41-65), buffer or nothing else was applied to the wounds. All wounds were dressed with paraffin gauze. The dressing was changed every two days for the first 10 days and twice a week for the next 30 days. Gel comprising peptide $\beta_1{}^{25}$ (41-65) and control gel were applied and wound measurements were made at each dressing change.

Excision wound model. Four pigs received intramuscular injection of ketamine, strenil® and atropine as described above. Six excision injuries were generated by removing full-thickness sections of skin (3×3 cm) from standardized sites on the back of each animal using a scapel. Three rabbits, were anesthetized by intramuscular injection of ketamine (5 mg/kg). Three excision injuries were produced in each by removing full-thickness sections of skin (0.5×1 cm) from each ear. After wounds, a thin layer of IntraSite® gel containing peptide $\beta_1{}^{25}$ (41-65) was applied to alternating wounds on each animal and IntraSite® gel+buffer was applied to the other half. The excision wounds were then dressed with a paraffin gauze. For pig experiments, the dressing was changed every two days for the first 10 days and twice a week for the next 30 days. For rabbit experiments, the dressing was changed for the first 3 days. Gel containing peptide $\beta_1{}^{25}$ (41-65) or control gel was applied at each dressing change.

Assessment of wound healing. Wound healing was assessed by evaluating the rates of wound re-epithelization and contraction. The open wound area and the area enclosed by the normal hair bearing skin were measured using the macrophotography technique (Ref. 14). The healing rate was monitored every two days for the first 10 days and twice a week for 30 more days. Wound reepithelialization as a percent of the original wound size was calculated using the following formula:

$$E = \frac{An - Ao}{An} \times 100$$

where E=rate of re-epithelialization in percent; An=area enclosed by the normal hair bearing skin on a given post-burn day; Ao=area of open wound on the same day as was measured. Wound contraction was calculated using the following formula:

$$C = \frac{A1 - An}{A1} \times 100$$

where C=rate of wound contraction in percent; A1=wound area as measured immediately following the burn or excision injury; An=area enclosed by normal hair bearing skin.

Immunohistochemistry. The wounds were frozen immediately after being removed from animals on post-excision day 30. Serial sections were placed on polylysine-coated slides. The sections containing wound areas were stained with hematoxylin/eosin and monoclonal antibodies to type I collagen and fibronectin and biotin-conjugated rabbit anti-mouse IgG/streptavidin-conjugated horseradish peroxidase (Ref. 16). The stained sections were examined and photographed by light microscopy.

Measurement of scar. The volumes of scar tissue were estimated by multiplying their thickness by the size of the scar on post-burn day 41 in pigs and post-excision day 10 in rabbits.

Experimental Results

The pig model is an art recognized model used in burn experiments because porcine skin is anatomically very similar to human skin (Ref. 15, 17). Pigs weighing about 20-25 kg were anesthetized by intramuscular injection of ketamine (5 mg/kg). A soldering iron with a flat contact area of ~20 cm was used to generate a full-thickness burn injury (110° C., 30 sec) on the skin of the back in four pigs. Six thermal burns (three on each side) were created on each pig. After wounding, two lesions were treated with a thin layer of a sterile IntraSite® gel containing peptide $\beta_1{}^{25}$ (41-65) (1.5 mM); two received gel alone and two received topical applications. All wounds were then bandaged and protected from potential contact irritation with a fixed frame. Peptide $\beta_1{}^{25}$ (41-65) and vehicle were applied every two days for the first 10 days and twice a week for the next 30 days, at which time the re-epithelialization and contraction of the wounds were measured and photographed as well. As used herein, the term "vehicle" refers generally to any solvent, buffer, gel or carrier in which the active peptide may be dispersed or dissolved, in the topical administration of peptide TGF-beta antagonists, the preferred vehicle is a gel, such as the IntraSite® gel comprising modified carboxymethyl-cellulose polymer and propylene glycol. Each animal served as its own control. As shown in FIG. 6A, skin burn wounds treated with peptide $\beta_1{}^{25}$ (41-65) exhibited rapid re-epithelialization and less contraction. The wounds showed significant re-epithelization and contraction after post-burn day 10. The re-epithelialization, which progressed from the surrounding wound margins toward center, appeared to be complete on post-burn day 26±2 (n=4) in wounds treated with peptide $\beta_1{}^{25}$ (41-65) whereas the wounds treated with vehicle showed 70±10% (n=4) re-epithelialization by this time (FIG. 6A). Healing of wounds treated without peptide $\beta_1{}^{25}$ (41-65) or vehicle was similar to that of the vehicle-only group. Wounds treated with peptide $\beta_1{}^{25}$ (41-65) exhibited less contraction than those treated with vehicle only (FIG. 6B). On post-burn day 33, cutaneous burns treated with peptide $\beta_1{}^{25}$ (41-65) and vehicle only exhibited 50±4 (n=4) and 70±2% (n=4) contraction, respectively (FIG. 6B). On post-burn day 34, the wounds treated with vehicle only exhibited a large area of open wound, whereas the wound treated with peptide $\beta_1{}^{25}$ (41-65) showed very little open wound (FIGS. 7C and D). On post-burn day 35, less scarring was seen in wounds treated with Peptide $\beta_1{}^{25}$ (41-65) than in the vehicle-only control wounds (FIG. 7 left E and F and FIG. 2 right E and F). The volumes of the scar tissue (on post-burn day 41) in wounds treated with peptide $\beta_1{}^{25}$ (41-65) and vehicle were 0.07±0.02 and 0.40±0.05 cm³, respectively. As before, the non-treated controls were indistinguishable from the vehicle-only group (data not shown). These results indicate that Peptide $\beta_1{}^{25}$ (41-65) treatment accelerates re-epithelialization and reduces scarring in the pig burn injury model.

Figure 8:
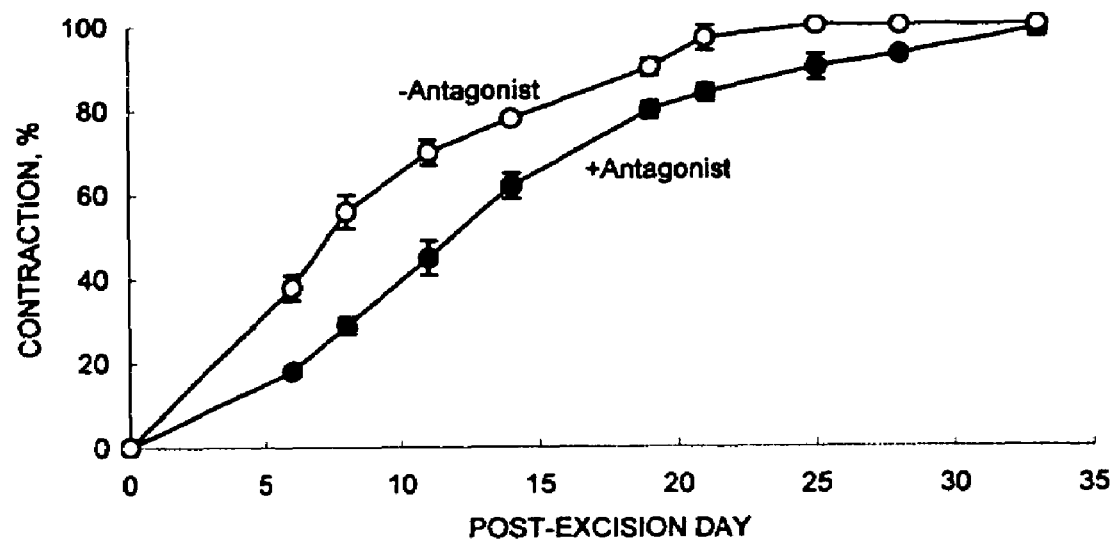
FIG. 8: Kinetics of contraction in pig excision wounds treated with TGF-β peptantagonist peptide TGF-beta antagonist). Excision wounds (3×3 cm) were treated with a TGF-β peptantagonist (peptide TGF-beta antagonist) and vehicle-only every two days for the first 10 days and twice a week for the next 30 days. The rate of wound contraction was determined as a percent of the original wound. Both the wounds treated with TGF-β peptantagonist (peptide TGF-beta antagonist) and vehicle only almost contracted completely in a horizontal direction (width of the healed wound) on post-excision day 41. The TGF-β peptantagonist-treated wound contracted vertically less than the control wound.
Figure 9:
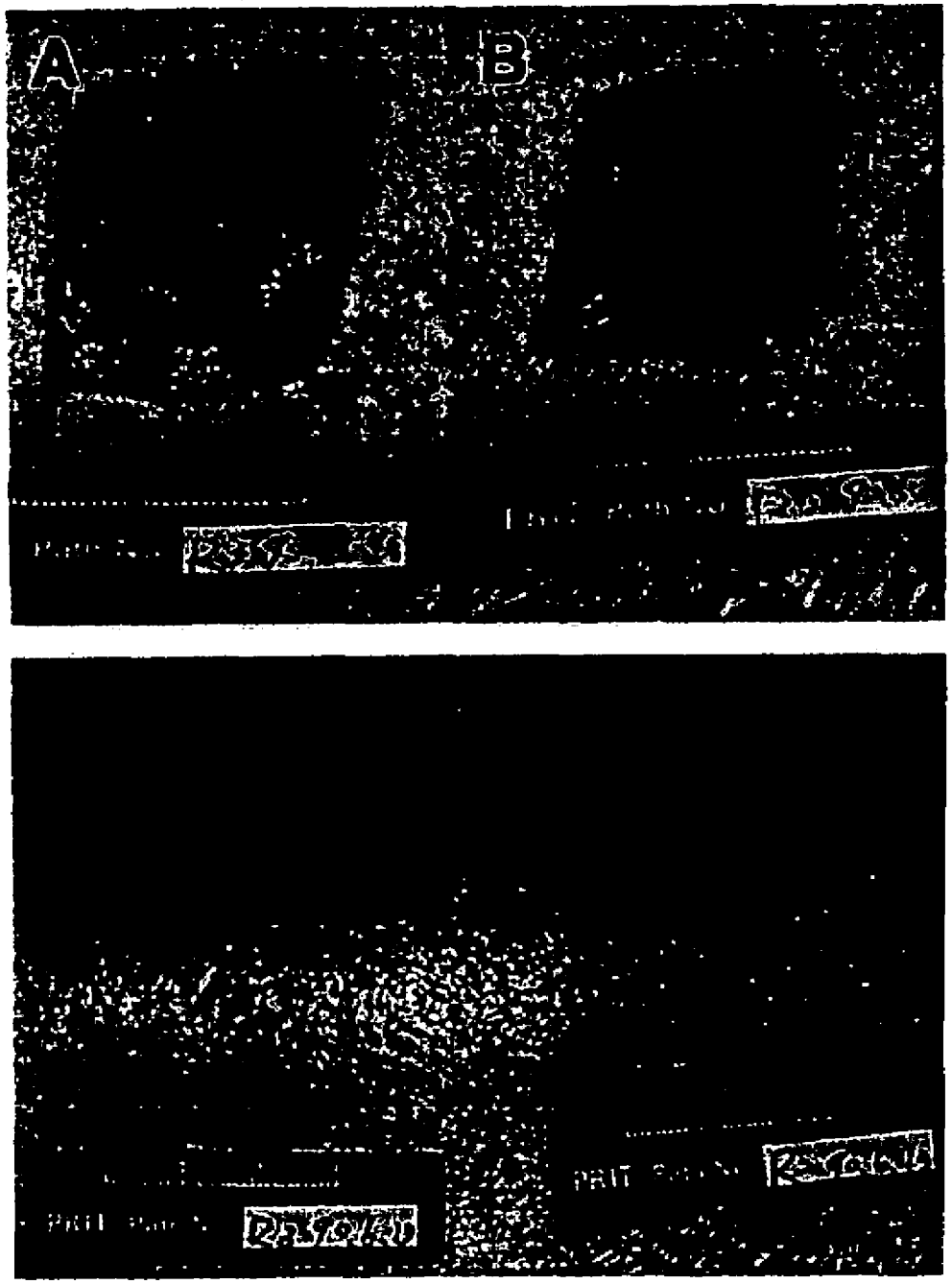
FIG. 9: Reduction of contraction in pig excision wounds treated with a TGF-β peptantagonist (peptide TGF-beta antagonist). Excision wounds (3×3 cm) on the back of pig skin were treated with a TGF-β peptantagonist (peptide TGF-beta antagonist) (panels A and C) and vehicle-only (panels B and D) every two days for the first 10 days and twice a week for the next 30 days. The wounds were photographed immediately after excision injury (panels A and B) and at post-wound day 34 (panels C and D). The TGF-β peptantagonist (peptide TGF-beta antagonist)-treated wound exhibited less vertical (length of the healed wound) contraction when compared with the control wound.

To test the effect of synthetic peptide $\beta_1{}^{25}$ (41-65) on scar formation after a different type of standardized injury in pigs, six full-thickness of skin (3×3 cm) were removed from the back of pigs. A thin layer of sterile gel containing peptide $\beta_1{}^{25}$ (41-65) (1.5 mM) or buffer was applied onto the wound immediately after the excision injury and every two days for the first 10 days and twice a week for the remaining experimental days. The dimensions of each wound were measured each time prior to the application of TGF-β peptantagonist or vehicle. The peptide $\beta_1{}^{25}$ (41-65) treatment attenuated contraction of the wound (FIG. 8). In contrast to the burn injury, the excision injury wound exhibited near complete horizontal (width of the healed wound) contraction by post-burn day 30 (FIG. 9). The wound treated with peptide $\beta_1{}^{25}$ (41-65) showed less vertical (length of the healed wound) contraction compared with that treated with vehicle only (FIGS. 9C and D). On post-incision day 41, less scar formation was observed in the wound treated with peptide $\beta_1{}^{25}$ (41-65) (FIGS. 9C and D).

Figure 10:
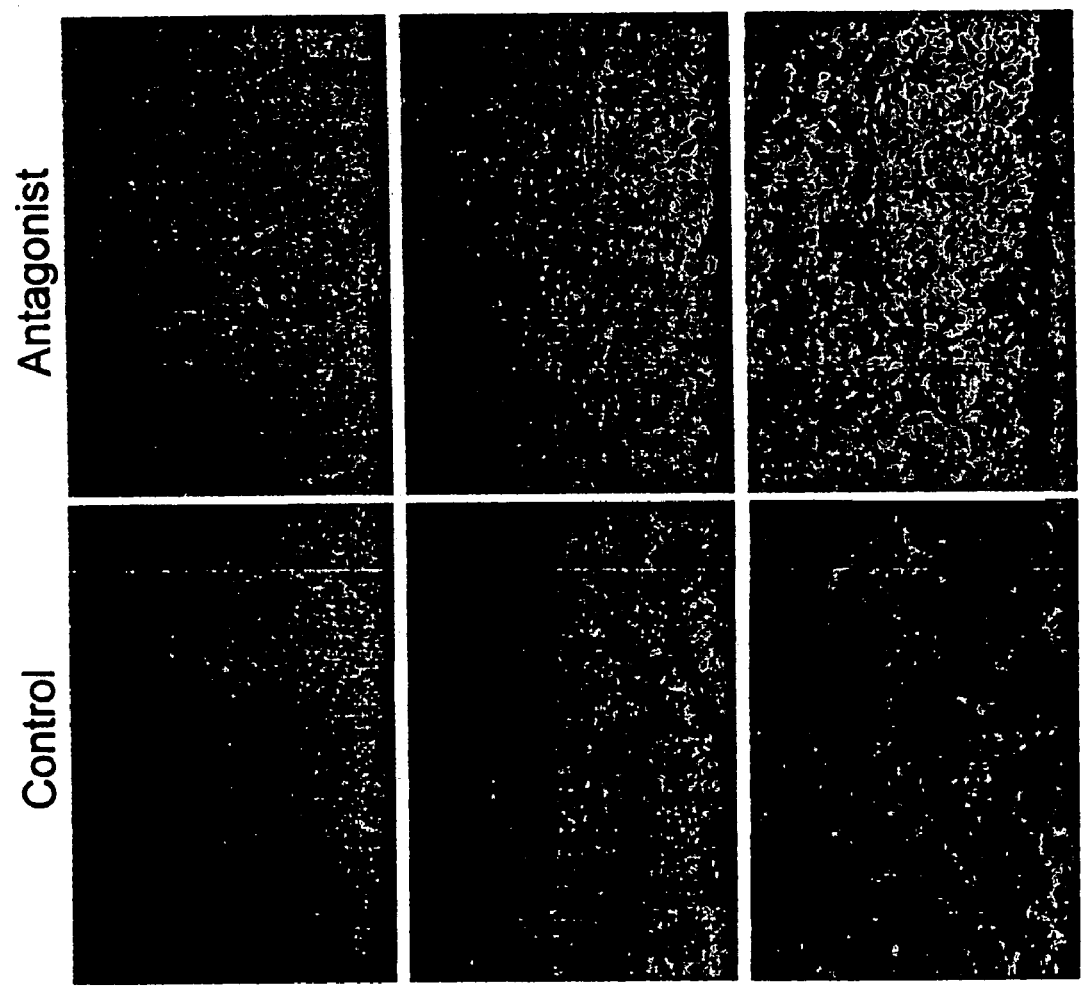
FIG. 10: Immunostaining for type I collagen and fibronectin of excision wounds in pigs. Sections of pig excision wounds treated with a TGF-β peptantagonist (peptide TGF-beta antagonist) (panels A, C and E), which were harvested on post-excision day 28, were histologically evaluated using hematoxylin/eosin staining (panels A and B) and were immunostained for type I collagen and fibronectin (panels C, D and E, F, respectively). The wound treated with a TGF-β peptantagonist (peptide TGF-beta antagonist) showed less intensity of staining for type I collagen and fibronectin than the control wound.

Accumulation of extracellular matrix proteins such as type I collagen and fibronectin is responsible for wound contraction and scar formation (Refs. 8-12). TGF-β is known to mediate the deposition of such extracellular matrix proteins by stimulating their biosynthesis and attenuating their degradation. Therefore, the content of type I collagen and fibronectin in excision-injury wounds (on post-excision day 30) in pigs was determined using immunohistochemistry. As shown in FIG. 10, peptide $\beta_1{}^{25}$ (41-65) treatment diminished the deposition of type I collagen and fibronectin (FIGS. 10C vs 10D and 10E vs 10F, respectively).

Figure 11:
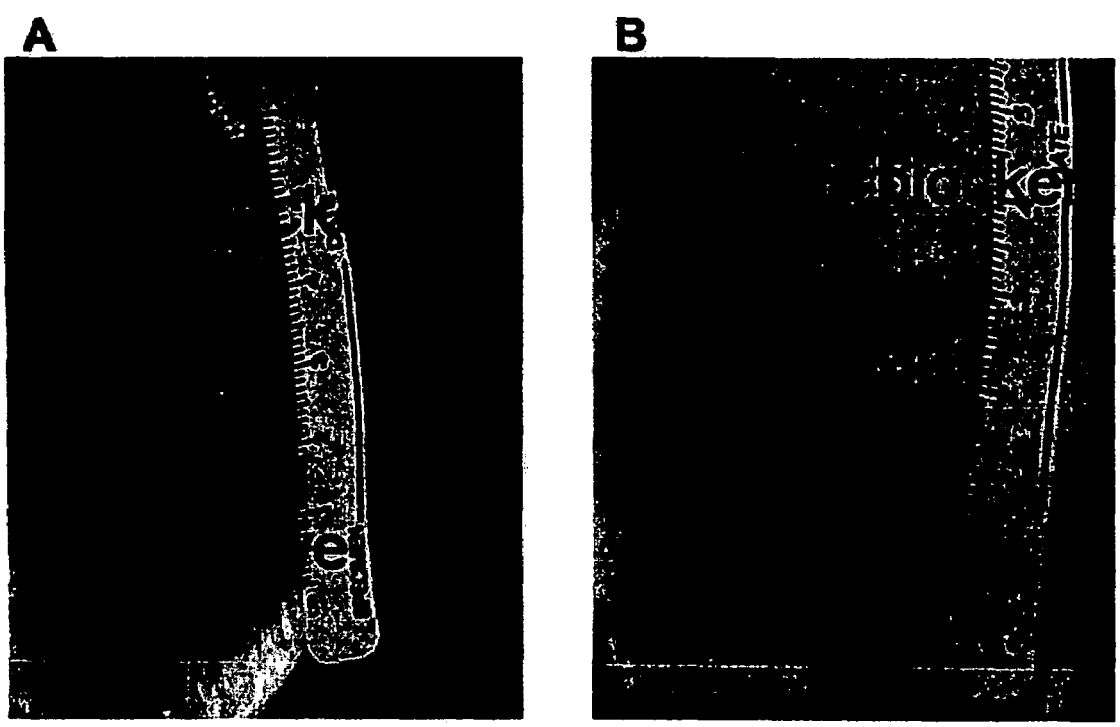
FIG. 11: Reduction of scarring in rabbit ear excision wounds treated with TGF-β peptantagonist (peptide TGF-beta antagonist). Excision wounds (0.5×1 cm) in rabbit ears were treated with a TGF-β peptantagonist (peptide TGF-beta antagonist) (TGF-blocker), vehicle only (sham) and nothing (negative). These wounds were photographed immediately after excision injury (panel A) and at post-excision day 10. The TGF-β-peptantagonist (peptide TGF-beta antagonist) treated wounds showed reduced scarring relative to the control wounds.

The effect of the peptide $\beta_1{}^{25}$ (41-65) was examined on scar formation after excision injury in the rabbit, which is another art-standard model of wound healing (Ref. 18). As shown in FIG. 11, the peptide $\beta_1{}^{25}$ (41-65) treatment attenuated scar formation after rabbit ear excision injury on post-excision day 10, whereas the wounds treated with vehicle only controls exhibited significant formation of scars. The volumes of scar tissue on post-excision day 10 in wounds treated with peptide $\beta_1{}^{25}$ (41-65), vehicle only, and without peptide $\beta_1{}^{25}$ (41-65) or vehicle were estimated to be 0.005±0.01 (n=6), 0.05±0.01 (n=6) and 0.04±0.02 (n=6) cm³, respectively. There were no apparent deleterious effects of peptide $\beta_1{}^{25}$ (41-65) or gel in any animal.

Thus it has been demonstrated that a specific synthetic peptide $\beta_1{}^{25}$ (41-65) accelerates re-epithelialization and reduces wound contraction and scarring in the pig burn injury model and diminishes wound contraction and scarring in both the pig and rabbit excision injury models. The finding that re-epithelialization is accelerated by the peptide $\beta_1{}^{25}$ (41-65) is somewhat unexpected. Burn wound healing consists of epithelialization, contraction and formation of granulation and scar tissue (Refs. 8-12). TGF-β is believed to be involved in most of these events. The antagonist peptide $\beta_1{}^{25}$ (41-65) is thought to block or slow down the occurrence of these events. The mechanism of enhanced re-epithelialization in wounds treated with the peptide $\beta_1{}^{25}$ (41-65) remains to be determined, but may involve increased keratinocyte proliferation (transient inhibition of keratinocyte proliferation by TGF-β may be an integral component in the complex process of wound healing) coupled with a migration response stimulated by growth factors other than TGF-β (Refs. 18-21). The peptide $\beta_1{}^{25}$ (41-65), which was recently shown to block complex formation between a2-macroglobulin and growth factors, cytokines and hormones (Ref. 22), may enhance activation of these substances or agents by blocking inhibition of their activities mediated by $\alpha_2$-macroglobulin.

What is claimed:

1. A non-naturally occurring peptide comprising SEQ ID NO. 12.

2. The peptide of claim 1, wherein said peptide is conjugated to a carrier protein.

3. The peptide of claim 2, wherein said carrier protein is bovine serum albumin or human carbonic anhydrase.

4. The peptide of claim 1, wherein said peptide is conjugated to a synthetic polymer.

* * * * *